United States Patent
Nguyen et al.

[11] Patent Number: 5,773,420
[45] Date of Patent: Jun. 30, 1998

[54] ACYLATED BENZYLGLYCOSIDES AS INHIBITORS OF SMOOTH MUSCLE CELL PROLIFERATION

[75] Inventors: Thomas T. Nguyen, Philadelphia, Pa.; John W. Ellingboe, Ridgewood, N.J.

[73] Assignee: American Home Products Corporation, Madison, N.J.

[21] Appl. No.: 531,142

[22] Filed: Oct. 20, 1995

[51] Int. Cl.$^6$ .............................. A61K 31/70; C07H 17/00
[52] U.S. Cl. .............................. 514/25; 514/53; 536/17.2; 536/17.9
[58] Field of Search ................................. 536/17.9, 17.2; 514/25, 53

[56] References Cited

U.S. PATENT DOCUMENTS

| | | | |
|---|---|---|---|
| 4,431,637 | 2/1984 | Upeslacis et al. | 514/25 |
| 4,754,025 | 6/1988 | Makise et al. | 536/17.7 |
| 5,011,923 | 4/1991 | Ono et al. | 536/17.9 |
| 5,019,562 | 5/1991 | Folkman et al. | 514/58 |

FOREIGN PATENT DOCUMENTS

| | | |
|---|---|---|
| 0312086 | 4/1989 | European Pat. Off. . |
| 0312087 | 4/1989 | European Pat. Off. . |
| 9309790 | 5/1993 | WIPO . |

OTHER PUBLICATIONS

Clowes, et al., J. Vasc. Surg. 13, 885–891 (1991).
Raines et al., Br. Heart J. 69 (Suppl.) S30 (1993).
Isik et al., Am. J. Pathol., 141 (5) 1139–1149 (1992).
Herrman et al., Drugs 46 (1), 18–52 (1993).
Herrman et al., Drugs 46 (1) 249–262 (1993).
Weissberg et al., Cardiovascular Res. 27 1191–1198 (1993).
Castellot et al., Seminars in Thrombosi and Hemostasis, 13(4), 489–503 (1987).
Borman, Chemical and Engineering News, p. 27, Jun. 28, 1993.
Reilly et al., Drug Development Research, 29, 137–147 (1993).
Zehavi et al., Carbohyd. Res. 151, 371–378 (1986).

Primary Examiner—Elli Peselev
Attorney, Agent, or Firm—Steven R. Eck

[57] ABSTRACT

This invention relates to acylated benzylglycosides and a method for their use as smooth muscle cell proliferation inhibitors and as therapeutic compositions for treating diseases and conditions which are characterize by excessive smooth muscle proliferation, such as restenosis. The acylated benzylglycosides of this invention are those of formula I, below:

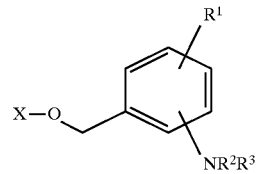

wherein X is

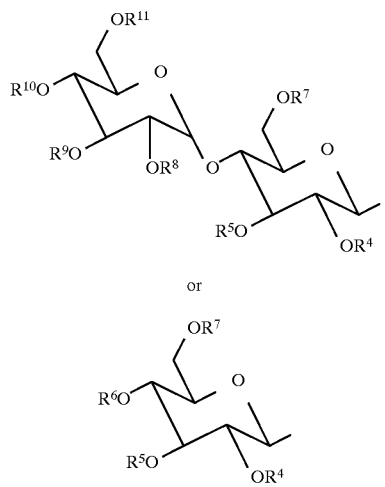

$R^1$ is H, alkyl having 1 to 6 carbon atoms, chloro, bromo, or alkoxy having 1 to 6 carbon atoms;

$R^2$ is H, an acyl group having 1 to 6 carbon atoms, phenylsulfonyl, or substituted phenylsulfonyl; and $R^3$ is an acyl group having 1 to 8 carbon atoms, benzoyl, substituted benzoyl, alkylsulfonyl having 1 to 6 carbon atoms, phenylsulfonyl, or substituted phenylsulfonyl;

$R^4$, $R^5$, $R^6$, $R^7$, $R^8$, and $R^9$ are each, independently, an acyl group having 1 to 6 carbon atoms; and $R^{10}$ and $R^{11}$ are each, independently, an acyl group having 1 to 6 carbon atoms, or the $R^{10}$ and $R^{11}$ groups on the 4' and 6' positions of the maltose or the 4 and 6 positions of the glucose form an isopropylidene group; or pharmaceutically acceptable salts thereof.

$R^4$, $R^5$, $R^6$, $R^7$, $R^8$, and $R^9$ are each, independently, an acyl group having 1 to 6 carbon atoms; and $R^{10}$ and $R^{11}$ are each, independently, an acyl group having 1 to 6 carbon atoms, or the $R^{10}$ and $R^{11}$ groups on the 4' and 6' positions of the maltose or the 4 and 6 positions of the glucose form an isopropylidene group; or a pharmaceutically acceptable salt thereof a pharmaceutically acceptable agent.

38 Claims, No Drawings

ACYLATED BENZYLGLYCOSIDES AS INHIBITORS OF SMOOTH MUSCLE CELL PROLIFERATION

This invention relates to acylated benzylglycosides. More particularly, this invention relates to novel acylated benzylglycosides and their use as smooth muscle cell proliferation inhibitors and as therapeutic compositions for treating diseases and conditions which are characterized by excessive smooth muscle proliferation, such as restenosis.

BACKGROUND OF THE INVENTION

All forms of vascular reconstruction such as angioplasty and vein bypass procedures effect a response to injury that ultimately leads to smooth muscle cell (SMC) proliferation and, subsequently, deposition of profuse amounts of extracellular matrix (Clowes, A. W.; Reidy, M. A. *J. Vasc. Surg* 1991, 13, 885). These events are also central processes in the pathogenesis of atherosclerosis (Raines E. W.; Ross R. *Br. Heart J.* 1993, 69 (Supplement), S 30) as well as transplant arteriosclerosis (Isik, F. F.; McDonald, T. O.; Ferguson, M.; Yamanaka, E.; Gordon *Am. J. Pathol.* 1992, 141, 1139). In the case of restenosis following angioplasty, clinically relevant solutions for controlling SMC proliferation through pharmacological intervention have remained elusive to date (Herrman, J. P. R.; Hermans, W. R. M.; Vos, J.; Serruys P. W. *Drugs* 1993, 4, 18 and 249). Any successful approach to selective SMC proliferation inhibition must not interfere with endothelial cell repair or the normal proliferation and function of other cells (Weissberg, P. L.; Grainger, D. J.; Shanahan C. M.; Metcalfe, J. C. *Cardiovascular Res.* 1993, 27, 1191).

The glycosaminoglycans heparin and heparan sulfate are endogenous inhibitors of SMC proliferation, yet are able to promote endothelial cell growth (Castellot, J. J. Jr.; Wright, T. C.; Karnovsky, M. J. *Seminars in Thrombosis and Hemostasis* 1987, 13, 489). However, the full clinical benefits of heparin, heparin fragments, chemically modified heparin, low molecular weight heparins, and other heparin mimicking anionic polysaccharides may be compromised due to other pharmacological liabilities (excessive bleeding arising from anticoagulation effects, in particular) coupled with heterogeneity of the various preparations (Borman, S. *Chemical and Engineering News*, 1993, Jun. 28, 27). Since the anticoagulant effects of many of these agents are independent of SMC antiproliferative activity, it would be expected that agents which are more homogenous in composition and of more defined molecular structure would exhibit a more desirable profile with fewer side effects associated with the aforementioned anionic polysaccharides. In the compounds of the present invention, the removal of sulfate groups has been found to depress anticoagulant effects but not affect antiproliferative activity.

PRIOR ART

Beta-Cyclodextrin tetradecasulfate has been described as a smooth muscle cell proliferation inhibitor and as an effective inhibitor of restenosis (Reilly, C. F.; Fujita, T.; McFall, R. C.; Stabilito, I. I.; Wai-si E.; Johnson, R. G. *Drug Development Research* 1993, 29, 137). U.S. Pat. No. 5019562 discloses anionic derivatives of cyclodextrins for treating pathological conditions associated with undesirable cell or tissue growth. WO 93/09790 discloses antiproliferative polyanionic derivatives of cyclodextrins bearing at least 2 anionic residues per carbohydrate residues. Meinetsberger (EP 312087 A2 and EP 312086 A2) describes the antithrombotic and anticoagulant properties of sulfated bis-aldonic acid amides. U.S. Pat. No. 4431637 discloses polysulfated phenolic glycosides as modulators of the complement system. The compounds of the present invention differ from all of the prior art in that the compounds (a) are benzylglycosides which bear no structural resemblance to heparin, sulfated cyclodextrins, or to sulfated lactobionic acid dimers, (b) contain no more than two contiguous sugar residues (dimer), (c) are of defined structure, (d) and are not sulfated.

Zehavi, U.; Herchman, M. *Carbohyd. Res.* 1986, 151, 371, discloses 4-carboxy-2-nitrobenzyl 4-O-α-D-glucopyranosyl-β-D-glucopyranoside which is attached to a polymer for study as an acceptor in the glycogen synthase reaction. The compounds of the present invention differ from those of the Zehavi disclosure in that (a) the substituents on the benzyl groups are different and (b) the use (smooth muscle antiproliferation) is different.

DESCRIPTION OF THE INVENTION

This invention describes the composition and utility of acylated benzylglycosides of formula I:

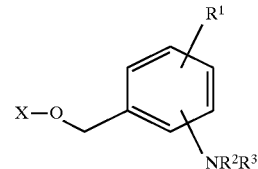

where X is

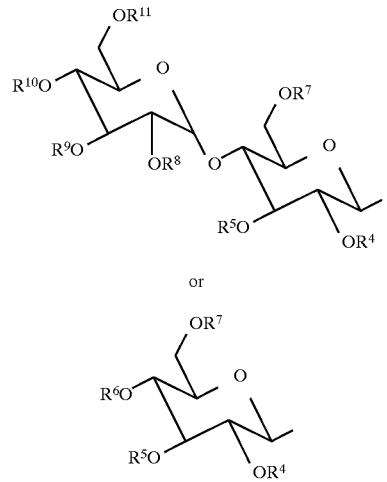

$R^1$ is H, alkyl having 1 to 6 carbon atoms, halo, $CF_3$, CN, $NO_2$, or alkoxy having 1 to 6 carbon atoms;

$R^2$ is H, an acyl group having 1 to 6 carbon atoms, phenylsulfonyl, or phenylsulfonyl substituted with $NO_2$; and $R^3$ is H, an acyl group having 1 to 8 carbon atoms, alkylsulfonyl having 1 to 6 carbon atoms, benzoyl, benzoyl substituted with $NH_2$, $NO_2$, CN, $C_1$–$C_6$ alkyl, $C_1$–$C_6$ alkoxy, $C_2$–$C_{15}$ acylamino, $CF_3$, $C_1$–$C_6$ alkanesulfonylamino, acetyl(methanesulfonyl)amino, halo, or OH, phenylsulfonyl, orphenylsulfonyl substituted with $C_1$–$C_6$ alkyl, $C_1$–$C_6$ alkoxy, $C_2$–$C_{15}$ acylamino, $NO_2$, CN, $CF_3$, $C_1$–$C_6$ alkanesulfonylamino, acetyl(methanesulfonyl)amino, OH, or halo;

$R^4$, $R^5$, $R^6$, $R^7$, $R^8$, and $R^9$ are each, independently, an acyl group having 1 to 6 carbon atoms; and $R^{10}$ and $R^{11}$ are each, independently, an acyl group having 1 to 6 carbon atoms, or the $R^{10}$ and $R^{11}$ groups on the 4' and 6' positions of the maltose or the 4 and 6 positions of the glucose form an isopropylidene group;

or pharmaceutically acceptable salts thereof.

A more preferred aspect or embodiment of this invention are the compounds of formula I:

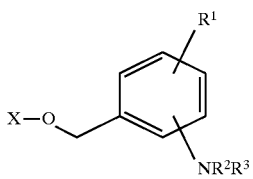

where X is

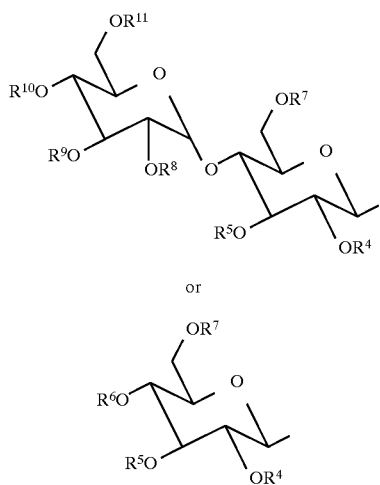

$R^1$ is H or alkyl having 1 to 6 carbon atoms;

$R^2$ is H, an acyl group having 1 to 6 carbon atoms, phenylsulfonyl, or 4-nitrophenylsulfonyl; and $R^3$ is H, an acyl group having 1 to 8 carbon atoms, benzoyl, benzoyl substituted with a nitro, amino, acetamido, 3,5-di-tert-butyl-4-hydroxybenzamido, cyano, or carbomethoxy group, alkylsulfonyl having 1 to 6 carbon atoms, phenylsulfonyl, or phenylsulfonyl substituted with a methanesulfonylamino, cyano, trifluoromethyl, alkoxy having 1 to 6 carbon atoms, alkyl having 1 to 6 carbon atoms, chloro, or nitro group;

$R^4$, $R^5$, $R^6$, R7, $R^8$, and $R^9$ are each, independently, an acyl group having 1 to 6 carbon atoms; and $R^{10}$ and $R^{11}$ are each, independently, an acyl group having 1 to 6 carbon atoms, or the $R^2$ groups on the 4' and 6' positions of the maltose or the 4 and 6 positions of the glucose form an isopropylidene group;

or pharmaceutically acceptable salts thereof.

The most preferred compounds of this invention are:

N-[2-methyl-5-(2,3,4,6-tetra-O-acetyl-β-D-glucopyranosyloxynethyl)phenyl]-3-nitrobenzamide or a pharmaceutically acceptable salt thereof;

3-amino-N-[2-methyl-5-(2,3,4,6-tetra-O-acetyl-β-D-glucopyranosyloxymethyl)-phenyl]benzamide hydrate or a pharmaceutically acceptable salt thereof;

5-(hepta-O-acetyl-β-maltosyloxymethyl)-2-methylphenylamine or a pharmaceutically acceptable salt thereof;

N-[5-(hepta-O-acetyl-β-D-maltosyloxymethyl)-2-methylphenyl]-3-nitrobenzamide or a pharmaceutically acceptable salt thereof;

N-[5-(hepta-O-acetyl-β-D-maltosyloxymethyl)-2-methylphenyl]-3-aminobenzamide or a pharmaceutically acceptable salt thereof;

3-acetylamino-N-[5-(hepta-O-acetyl-β-D-maltosyloxymethyl)-2-methylphenyl]-benzamide or a pharmaceutically acceptable salt thereof;

N-{3-[2-(hepta-O-acetyl-β-D-maltosyloxymethyl)-6-methylphenylcarbamoyl]phenyl}-3,5-di-tert-butyl-4-hydroxybenzamide or a pharmaceutically acceptable salt thereof;

N-[5-(hepta-O-acetyl-β-D-maltosyloxymedyl)-2-methylphenyl]-3-cyanobenzamide or a pharmaceutically acceptable salt thereof;

N-[5-(hepta-O-acetyl-β-D-maltosyloxymethyl)-2-methylphenyl]-5-nitroisophthalamic acid methyl ester or a pharmaceutically acceptable salt thereof;

N-[5-(hepta-O-acetyl-βp-D-maltosyloxymethyl)-2-methylphenyl]acetamide or a pharmaceutically acceptable salt thereof;

N-[5-(hepta-O-acetyl-β-D-maltosyloxymethyl)-2-methylphenyl]propionamide or a pharmaceutically acceptable salt thereof;

pentanoic acid N-[5-(hepta-O-acetyl-β-D-maltosyloxymethyl)-2-methylphenyl]amide or a pharmaceutically acceptable salt thereof, N-[5-(hepta-O-acetyl-β-D-maltosyloxymethyl)-2-methylphenyl]-2,2-dimethyl- propionamide or a pharmaceutically acceptable salt thereof;

cyclopropanecarboxylic acid N-[5-(hepta-O-acetyl-β-D-maltosyloxymethyl)-2-methylphenyl]amide or a pharmaceutically acceptable salt thereof;

cyclopentanecarboxylic acid N-[5-(hepta-O-acetyl-β-D-maltosyloxymethyl)-2-methylphenyl]amide or a pharmaceutically acceptable salt thereof;

N-[5-(hepta-O-acetyl-β-D-maltosyloxymethyl)-2-methylphenyl]-3-cyclopentylpropionamide or a pharmaceutically acceptable salt thereof;

N-[5-(hepta-O-acetyl-β-D-maltosyloxymethyl)-2-methylphenyl]-4-(methanesulfonylamino) benzenesulfonamnide or a pharmaceutically acceptable salt thereof;

N-[5-(hepta-O-acetyl-β-D-maltosyloxymethyl)-2-methylphenyl]-4-cyanobenzenesulfonamide or a pharmaceutically acceptable salt thereof;

N-[5-(hepta-O-acetyl-β-D-maltosyloxymethyl)-2-methylphenyl]-4-trifluoromethylbenzenesulfonamide or a pharmaceutically acceptable salt thereof;

N-[5-(hepta-O-acetyl-β-D-maltosyloxymethyl)-2-methylphenyl]-3-trifluoromethylbenzenesulfonamide or a pharmaceutically acceptable salt thereof;

N-[5-(hepta-O-acetyl-β-D-maltosyloxymethyl)-2-methylphenyl]-2-trifluoromethylbenzenesulfonamnide or a pharmaceutically acceptable salt thereof;

N-[5-(hepta-O-acetyl-β-D-maltosyloxymethyl)-2-methylphenyl]-3-(methanesulfonylamino) benzenesulfonarnide or a pharmaceutically acceptable salt thereof;

N-[5-(hepta-O-acetyl-p-D-maltosyloxymethyl)-2-methylphenyl]-4-methoxybenzenesulfonamide or a pharmaceutically acceptable salt thereof;

N-[5-(hepta-O-acetyl-β-D-maltosyloxymethyl)-2-methylphenyl]-4-methylbenzenesulfonamide or a pharmaceutically acceptable salt thereof;

N-[5-(hepta-O-acetyl-β-D-maltosyloxymethyl)-2-methylphenyl]-4-chlorobenzenesulfonamide or a pharmaceutically acceptable salt thereof;

N-[5-(hepta-O-acetyl-β-D-maltosyloxymethyl)-2-methylphenyl]-4-chloro-3-nitrobenzenesulfonamide or a pharmaceutically acceptable salt thereof;

N-[5-(hepta-O-acetyl-β-D-maltosyloxymethyl)-2-methylphenyl]methanesulfonamide or a pharmaceutically acceptable salt thereof;

butane-1-sulfonic acid N-[5-(hepta-O-acetyl-β-D-maltosyloxymethyl)-2-methylphenyl]amide or a pharmaceutically acceptable salt thereof;

4-(hepta-O-acetyl-β-D-maltosyloxymethyl)-2-methylphenylarnine hydrochloride or a pharmaceutically acceptable salt thereof;

N-[44epta-O-acetyl-β-D-maltosyloxymethyl)-2-methylphenyl] -4-(methanesulfonylamino)benzenesulfonamide or a pharmaceutically acceptable salt thereof;

N-[4-(hepta-O-acetyl-β-D-maltosyloxymethyl)-2-methylphenyl]-4-nitro-N-(4-nitrophenylsulfonyl)benzenesulfonamide or a pharmaceutically acceptable salt thereof;

N-acetyl-4-[acetyl(methanesulfonyl)amino]-N-[5-(4',6'-O-isopropylidine-2,2',3,3',6-penta-O-acetyl-β-D-maltosyloxymethyl)-2-methylphenyl]benzenesulfonamide or a pharmaceutically acceptable salt thereof;

N-propionyl-4-[propionyl(methanesulfonyl)amino]-N-[5-(hepta-O-propionyl-β-D-maltosyloxymethyl)-2-methylphenyl]benzenesulfonamide or a pharmaceutically acceptable salt thereof.

PROCESS OF THE INVENTION

The compounds of the present invention can be prepared according to the general sequence of reactions outlined in the Schemes below:

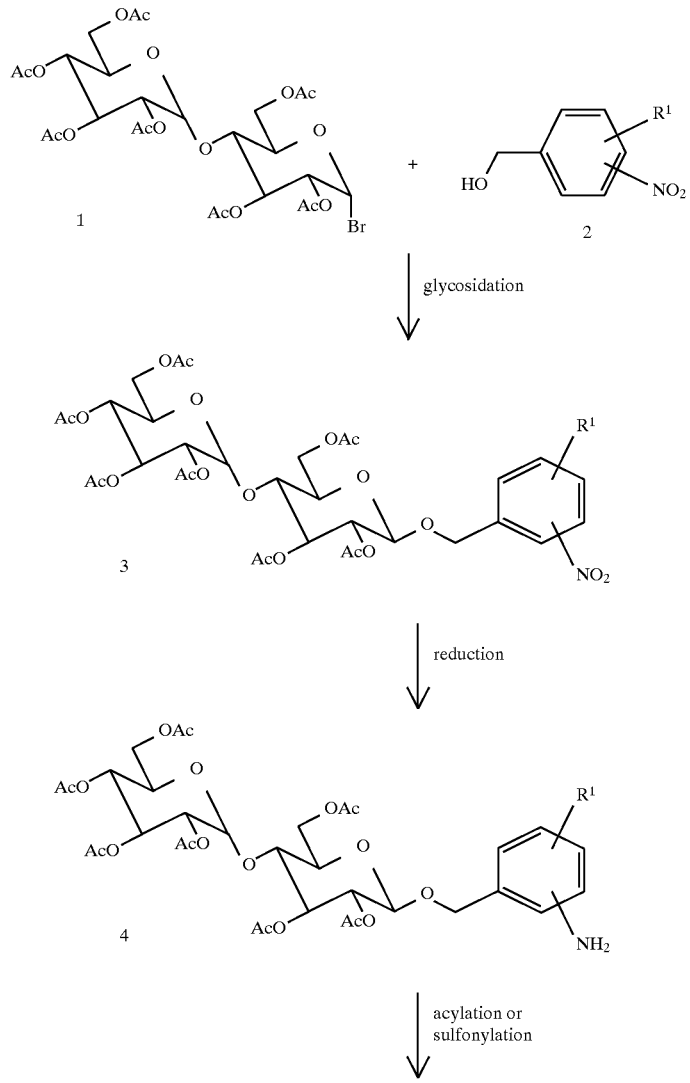

Scheme I

Scheme I

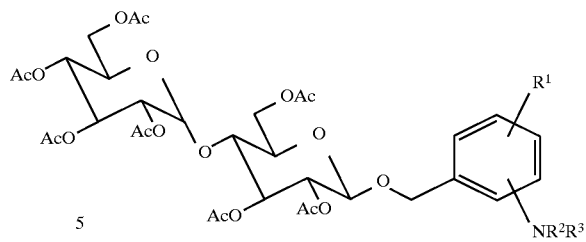

where $R^1$, $R^2$, and $R^3$ are as defined above.

Thus, maltosyl bromide 1 is coupled with a benzyl alcohol 2 in the presence of a catalyst such as a mercuric bromide, mercuric cyanide, silver triflate, or silver perchlorate in an aprotic solvent such as dichloromethane, ether, toluene, or nitromethane at temperatures ranging from −40° C. to reflux to yield glycoside 3. Reduction of the nitro group of 3 can be accomplished with a reducing agent such as stannous chloride in a polar aprotic solvent such as ethyl acetate at ambient temperature to reflux, or by catalytic hydrogenation in the presence of a catalyst such as palladium on carbon gives an anilino compound 4. Coupling of 4 with an acid chloride or sulfonyl chloride can be completed in the presence of an amine base such as triethylamine or diisopropylethylamine in an aprotic solvent such as dichloromethane or tetrahydrofuran at temperatures ranging from −20° C. to ambient temperature yields the target compounds 5. The same sequence of reactions can be used starting with bromoglucose tetraacetate to yield the glucose analogue of 5.

Scheme II

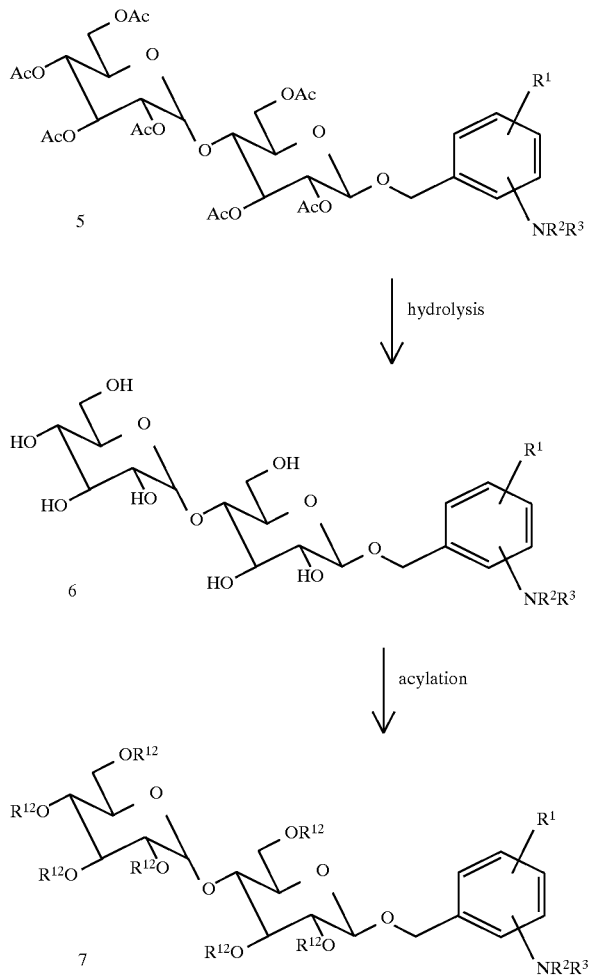

-continued
Scheme II

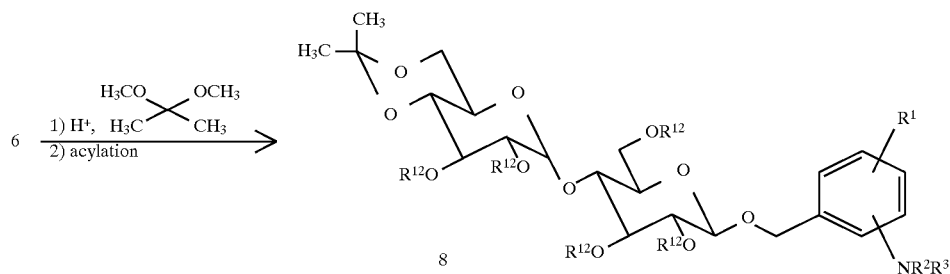

As illustrated in Scheme II, wherein $R^1$, $R^2$ and $R^3$ are as defined above and $R^{12}$ is an acyl group having from 1 to 6 carbon atoms, the acetate groups of 5 can be replaced by hydrolysis with a base such as sodium methoxide in methanol or aqueous sodium hydroxide in methanol at ambient temperature to reflux to yield 6 and reacylation with an acyl anhydride in the presence of an amine base such as pyridine at temperatures ranging from 0° C. to ambient temperature to yield 7. Alternatively, after hydrolysis of the acetate groups, the 4 and 6 hydroxy groups of glucose or the 4' and 6' hydroxy groups of maltose can be reacted with dimethoxypropane in the presence of an acid catalyst such as camphorsulfonic acid in a polar aprotic solvent such as acetonitrile at ambient temperature to yield an isopropylidene derivative 8.

This invention is also directed to pharmaceutical compositions comprised of acylated benzylglycosides either alone or in combination with excipients (i.e. pharmaceutically acceptable materials with no pharmacological effect). Such compositions are useful for diseases or conditions which are characterized by excessive smooth muscle cell proliferation most frequently arising from vascular reconstructive surgery and transplantation, for example, balloon angioplasty, vascular graft surgery, coronary artery bypass surgery, and heart transplantation. Other disease states in which there is unwanted vascular proliferation include hypertension, asthma, and congestive heart failure. The compounds of the invention are thus useful for treating these diseases and states.

The compounds of this invention may be administered systemically, for example by intravenous injection, typically ranging from 0.1 to 10 mg/kg/h over 5–30 days, or by subcutaneous injection at lower dose, by oral administration at higher dose than intravenous injection. Localized delivery of the compounds of this invention may also be achieved by transmembrane, transdermal, or other topical administrative routes using appropriate continuous release devices such as supporting matrix, where applicable. The compositions of the invention may be formulated with conventional excipients, such as a filler, a disintegrating agent, a binder, a lubricant, a flavoring agent and the like. These are formulated in a conventional manner. It is understood that the compounds of this invention may be administered in any manner and at any concentration that is efficacious to the particular recipient. The manner of delivery and composition and concentration of the pharmaceutical dose will be determined on an individual basis by the physician or other skilled medical professional treating the recipient.

EFFECTS ON CELL PROLIFERATION

A. Cell Sources

The ability of the compounds of the present invention to inhibit smooth muscle cell proliferation was established using isolated aortic cells. Porcine aortas were received from a local slaughterhouse and were iced during transit. The aorta was scrupulously cleansed of fatty tissue and rinsed in sterile phosphate-buffered saline with 2% antibiotic/antimycotic (Gibco catalog #600–5240 AG). The tissue was then digested in 10–15 mL of "Enzyme Mixture" containing collagenase type I, 165 U/mL; elastase type III, 15 U/mL; BSA, 2 mg/mL; and soybean trypsin inhibitor, 0.375 mg/mL followed by incubation at 37° C. under 5% $CO_2$ for 10–15 min. After this treatment, the outer surface adventitia was easily removed by peeling with forceps. The aorta was then longitudinally cut and laid open and the endothelial layer was removed by scraping.

The medial layer of cells was rinsed in enzyme solution, and placed in a new 100 mm dish with 10 mL of enzyme solution. The aorta was minced using a fine pair of scissors and digested for 2–3 h at 37° C. in 30 mL of fresh enzyme solution. After digestion, the tissue was homogenized using a sterile Pasteur pipette with a fire polished tip or an eppendorf pipetter with a 200–1000 μL sterile pipette tip. The suspension was then centrifuged for 10 minutes at 8000 rpm and the pellet was suspended in 4–6 mL of fresh medium and plated onto 4–6 100 mm flasks with vented caps. Cells were allowed to grow to confluence and split using 0.25% trypsin. Cells were evaluated for purity and overall quality using antibody to SMC actin.

B. Examination of the Effects of Compounds on Cell Proliferation Using $^3H$ Thymidine Incorporation Cells were assayed in early passage (generally passage 3–7) at sub-confluent conditions. Cultures were grown in 16 mm (24 well) multi-well culture dishes in medium 199 supplemented with 10% fetal bovine serum and 2% antibiotic/antimycotic. At subconfluence, the cells were placed in a defined serum free medium (AIM-V; Gibco) for 24–48 h prior to initiating the experimental protocol.

Although compounds were found to be more effective with longer pre-incubations, in general, experiments were initiated with the addition of compound, $^3H$ thymidine and serum / growth factor to serum deprived synchronized cells and results are reported in this invention accordingly.

Compounds were added to each well at 50 fold dilution (20 μL / well) and the plates were incubated for 24–36 h at 37° C. in 5% $CO_2$. Compounds were initially dissolved in 50% ethanol and serially diluted into media. Compounds were routinely assayed at concentrations from 1 to 100 μM. As a control, grade II porcine intestinal mucosal heparin (sodium salt) from Sigma (H-7005) was routinely assayed in all cell preparations at concentrations from 0.1 to 100 μg/iL.

At the completion of the experiment, plates were placed on ice, washed three times with ice cold phosphate buffered saline (PBS) and incubated in ice cold 10% trichloroacetic acid (TCA) for 30 minutes to remove acid soluble proteins. Solution was transferred to scintillation vials containing 0.4

N HCl (500 μL/vial to neutralize NaOH) and each well was rinsed two times with water (500 μL) for a total volume of 2 mL/vial.

Data was obtained, in triplicate, for both control and experimental samples. Control (100%) data was obtained from maximally stimulated cells, as the result of growth factor or serum stimulation. Experimental data was obtained from cells maximally stimulated with growth factor or serum and treated with compound. Data was expressed as a percent of control from which a percent inhibition or $IC_{50}$ could be determined. Results for the compounds of Examples 1–33 for serum stimulated assays are reported in Table I below.

C. Cytotoxicity

Visually, all cells were found to tolerate high levels of all compounds quite well, however to insure that no toxicity was present, cytotoxicity of compounds was examined using a commercial modification of the MTT (3-[4,5-dimethylthiazol-2-yl]-2,5-diphenyltetrazolium bromide) assay. Briefly, cells were again grown in 24 well plates to 70–80% confluency and, as before, serum deprived for 24–48 h prior to initiation of the experimental protocol. To insure that the MTT assay monitored toxicity rather than proliferation, cells were incubated with 100 μg/mL of drug in fresh medium without serum for 24 h at 37° C. in a humidified $CO_2$ incubator. Upon completion of the compound treatment, MTT (3-[4,5-dimethylthiazol-2-yl]-2,5-diphenyltetrazolium bromide) indicator dye was added for 4 h at 37° C. Cells were then lysed and aliquots from each well were transferred to a 96 well plate for analysis. Absorbance at 570 nm wavelength with a reference wavelength of 630 nm was recorded using an ELISA plate reader. Results were determined as percent viable using no drug (100% viable) and pre-solubilization (0% viable) standards. The compounds of Examples 3, 6, 11, 12, 14, 15, 16, and 17 exhibited no toxicity at up to 100 μg/mL.

ANTICOAGULANT ACTIVITY

The anticlotting activity of the compounds of this invention was evaluated in a partial thromboplastin time (APTT) assay using normal human plasma collected from 5 donors according to the procedure of Fenichel et. al. (*Clin. Chem.* 1964, 10, 69). A BBL Fibrometer automatic precision coagulation timer utilizing a 0.3 mL probe was employed. An Ellagic acid activated partial thromboplastin was used for these experiments. This reagent was added to human citrated plasma equilibrated at 37° C. in a plastic well in the clot timer. Calcium at 37° C. was added, the clot timer was started and the time for fibrin clot formation (in seconds) was recorded. The effect of the compounds, added to plasma, over a concentration of 12.5–200 μg/mL was determined. Any plasma which did not clot after 240 seconds was assigned a clotting time of 240 seconds. An unfractionated heparin comparator was used over the concentration range of 1.25–10 μg/mL. Clotting tests at all concentrations were run in triplicate. Analysis of variance for a randomized block design was used to determine the significance of differences observed in the clotting times. The compounds of this invention showed no anticoagulation activity at concentrations up to 200 μg/mL.

TABLE I

Smooth Muscle Antiproliferation Activity and Anticoagulation Activity

| Compound of Example | Porcine Smooth Muscle Cell Antiproliferation $IC_{50}$ or (% Inhibition at x concentration) |
|---|---|
| 1 | 79% inhibition at 50 μg/mL |
| 2 | 23% inhibition at 50 μg/mL |
| 3 | 5.08 μM |
| 4 | 13% inhibition at 50 μg/mL |
| 5 | 44% inhibition at 50 μg/mL |
| 6 | 18.3 μM |
| 7 | 185.4 μM |
| 8 | 37.1 μM |
| 9 | 14.6 μM |
| 10 | 64.0 μM |
| 11 | 20.4 μM |
| 12 | 4.8 μM |
| 13 | 44.3 μM |
| 14 | 48.4 μM |
| 15 | 46.7 μM |
| 16 | 37.8 μM |
| 17 | 26.5 μM |
| 18 | 29.0 μM |
| 19 | 4.0 μM |
| 20 | 9.3 μM |
| 21 | 40.0 μM |
| 22 | 25.4 μM |
| 23 | 28.0 μM |
| 24 | 61% inhibition at 40 μM |
| 25 | 10.0 μM |
| 26 | 23.1 μM |
| 27 | 22.4 μM |
| 28 | 9.0 μM |
| 29 | 70% inhibition at 40 μM |
| 30 | 13.8 μM |
| 31 | 37% inhibition at 100 μM |
| 32 | 6.2 μM |
| 33 | 30% inhibition at 20 μM |
| heparin (H-7005) | 45–83% inhibition at 50 μg/mL |

The compounds of Examples 3, 11, 12 and 17 exhibited no anticoagulant activity (APTT assay).

Specific procedures are described in the following examples. These examples are given to illustrate the invention and should not be construed as limiting the invention set forth in the appended claims.

EXAMPLE 1

N-[2-Methyl-5-(2,3,4,6-tetra-O-acetyl-β-D-glucoivranosyloxymethyl)phenyl]-3-nitrobenzamide Step 1

N-(5-Hydroxymethyl-2-methylphenyl)-3-nitrobenzamide

To a stirred, cooled (0° C.) mixture of 3-amino-4-methylbenzyl alcohol (10.0 g, 0.072 mol) and pyridine (5.8 g, 0.072 mol) in THF (100 ML) was added 3-nitrobenzoyl chloride (13.5 g, 0.072 mol). After 2 h, the mixture was concentrated, suspended in water and filtered to give a brown solid. Trituration with hot EtOH gave 18.8 g (90%) of product as a white solid, mp 198°–200° C.; $^1$H NMR (DMSO-$d_6$) δ 2.20 (s, 3 H), 4.46 (s, 2 H), 7.12 (dd, J=7.8 Hz, 1.5 Hz, 1 H), 7.25 (dd, J=7.8, 1.5 Hz, 1 H), 7.82 (m, 1 H), 8.41 (m, 2 H), 8.78 (s, 1 H), 10.26 (s, 1 H).

Step 2

N-[2-Methyl-5-(2,3,4,6-tetra-O-acetyl-β-D-glucopyranosyloxymethyl)-phenyl]-3-nitrobenzamide A mixture of N-(5-hydroxymethyl-2-methylphenyl)-3-nitrobenzamide (10.0 g, 0.034 mol), $HgBr_2$ (10.0 g, 0.041 mol), Hg(CN)$_2$ (15.0 g, 0.058 mol), and α-D-glucopyranosyl bromide tetraacetate (17.2 g, 0.042 mol) in nitromethane (200 mL) was heated under reflux for 4 h. 2.0M KBr was added and the mixture was stirred for 30 minutes and extracted with EtOAc. The combined extracts were washed with saturated aqueous NaHCO$_3$ and brine, dried (MgSO$_4$), and concentrated to give 12.0 g (56%) of product as a brown foam; $^1$H NMR (DMSO-d$_6$) δ2.00 (m, 12 H), 2.21 (s, 3 H), 4.00 (m, 2 H), 4.20 (dd, J=12.4, 5.0 Hz, 1 H), 4.58 (d, J=12.4 Hz, 1 H), 4.82 (m, 4 H), 5.27 (t, J=9.3 Hz, 1 H), 7.10 (d, J=7.8 Hz, 1 H), 7.24 (d, J=7.8 Hz, 1 H), 7.25 (s, 1 H), 7.81 (m, 1 H), 8.42 (m, 2 H), 8.80 (s, 1 H), 10.60 (s, 1 H).

EXAMPLE 2

3-Amino-N-[2-methyl-5-(2,3,4,6-tetra-O-acetyl-β-D-glucolvranosyloxymethyl)Rhenyl]benzamide Hydrate A solution of N-[2-methyl-5-(2,3,4,6-tetra-O-acetyl-β-D-glucopyranosyloxy-methyl)phenyl]-3-nitrobenzamide (2.0 g, 3.244 mmol), prepared as described in Example 1, in MeOH (15 mL) was hydrogenated over 10% Pd/C (1.0 g) at atmospheric pressure for 18 h. The mixture was filtered through solka floc and the filtrate was concentrated. Purification by flash chromatography (1% MeOH/CH$_2$Cl$_2$) gave 1.30 g (68%) of product as a white solid, mp 94°–96° C.; $^1$H NMR (DMSO-d$_6$) δ 2.00 (m, 12 H), 2.21 (s, 3 H), 4.03 (m, 1 H), 4.06 (d, J=2.3 Hz, 1 H), 4.20 (dd, J=12.4, 5.0 Hz, 1 H), 4.55 (d, J=12.4 Hz, 1 H), 4.75 (d, J=12.4 Hz, 1 H), 4.90 (m, 3 H), 5.27 (t, J=9.3 Hz, 1 H), 5.28 (s, 2 H), 6.72 (m, 1 H), 7.10 (m, 4 H), 7.23 (d, J=7.9 Hz, 1 H), 7.27 (d, J=1.45 Hz, 1 H), 9.63 (s, 1 H).

EXAMPLE 3

5-(Heita-O-acetyl-δ-maltosyloxymethyl)-2-methylihenylamine Hydrochloride

Step 1

5-(Hepta-O-acetyl-β-maltosyloxymethyl)-2-methyl-1-nitrobenzene

To a mixture of 4-methyl-3-nitrobenzyl alcohol (4.0 g, 24.0 mmol) and acetobromo-α-maltose (20.0 g, 29.0 mmol) in CH$_3$NO$_2$ (60 mL) was added Hg(CN)$_2$ (6.15 g, 24.0 mmol) and HgBr$_2$ (6.91 g, 19.0 mmol). After stirring at ambient temperature overnight, brine was added and the mixture was stirred for 20 min. The reaction mixture was extracted with CH$_2$Cl$_2$. The organic phase was washed with brine, dried (MgSO$_4$), and concentrated. Purification by flash chromatography (1:2 and 1:1 EtOAc / petroleum ether) and rechromatography using ether / petroleum ether (3:1, then 4:1, then 100:0) gave 7.97 g of the title compound as a colorless solid; $^1$H NMR (CDCl$_3$) δ2.00 (s, 3 H), 2.01 (s, 3 H), 2.03 (s, 6 H), 2.04 (s, 3 H), 2.11 (s, 3 H), 2.16 (s, 3 H), 2.60 (s, 3 H), 3.65–3.71 (m, 1 H), 3.9–4.1 (m, 3 H), 4.2–4.3 (m, 2 H), 4.54 (dd, 1 H), 4.62 (d, 1 H), 4.65 (d, 1 H), 4.8–5.0 (m, 3 H), 5.06 (t, 1 H), 5.25 (t, 1 H), 5.25 (t, 1 H), 5.36 (t, 1 H), 5.42 (d, 1 H), 5.42 (d, 1 H), 7.32 (d, 1 H), 7.41 (d, 1 H), 7.92 (s, 1 H).

Step 2

5-(Hepta-O-acetyl-β-maltosyloxymethyl)-2-methylphenylamine Hydrochloride

Procedure A:

A mixture of 5-(hepta-O-acetyl-β-maltosyl-oxymethyl)-2-methyl-1-nitrobenzene (4.0 g, 5.1 mmol) and SnCl$_2$•H$_2$O (8.00 g, 35.0 mmol) in EtOAc (100 mL) was heated under reflux for 2 h. The reaction mixture was cooled to room temperature and saturated aqueous NaHCO$_3$ was added. After stirring for 15 minutes, the mixture was diluted with CH$_2$Cl$_2$ (200 ML) and filtered through solka floc. The organic phase was dried (MgSO$_4$) and concentrated. Purification by flash chromatography (EtOAc / CH$_2$Cl$_2$, 1:5, then 1:4, then 1:2, then 1:1) gave 3.42 g (89%) of 5-(hepta-0-acetyl-β-maltosyloxymethyl)-2-methylphenylamine as a colorless foam; $^1$H NMR (CDCl$_3$) δ 1.99 (s, 6 H), 2.00 (s, 3 H), 2.03 (s, 6 H), 2.11 (s, 3 H), 2.17 (s, 6 H), 3.63–3.67 (m, 1 H), 3.95–4.01 (m, 3 H), 4.26 (dd, 2 H), 4.51 (d, 1 H), 4.54 (d, 1 H), 4.75 (d, 1 H), 4.82–4.90 (m, 2 H), 5.05 (t, 1 H), 5.20 (t, 1 H), 5.39 (t, 1 H), 5.41 (d, 1 H), 6.62 (d, 1 H), 6.63 (s, 1 H), 7.01 (d, 1 H).

A hydrochloride salt was prepared by treating a solution of similarly prepared free base (5.94 g, 7.86 mmol) in ether (300 mL) with saturated ethereal HCl (100 mL). The precipitate was collected by filtration to give 4.83 g (78%) of the title compound as a white solid, mp 124–130° C.

Procedure B:

A solution of 5-(hepta-O-acetyl-β-maltosyl-oxymethyl)-2-methyl-1-nitrobenzene (31.1 g, 39.6 mmol) was hydrogenated at 50 psi over 10% Pd/C (10.0 g) for 1 h. The catalyst was removed by filtration and the filtrate was concentrated to give a white foam. Trituration with water gave 28.0 g (94%) of 5-(hepta-O-acetyl-β-maltosyloxymethyl)-2-methylphenylamine as a white solid, mp 154–156° C.

EXAMPLE 4

N-[5-(Helta-O-acetyl-β-D-maltosyloxymethy:)-2-methyllhenyl]-3-nitrobenzamide

To a stirred mixture of 5-(hepta-O-acetyl-β-maltosyloxymethyl)-2-methylphenylamine (1.90 g, 2.52 mmol), prepared according to Example 3, and pyridine (0.22 g, 2.77 mmol) in CH$_2$Cl$_2$ (10 mL) was added 3-nitrobenzoyl chloride (0.51 g, 2.77 mmol). After 18 h, the mixture was diluted with EtOAc, washed with saturated aqueous NaHCO$_3$, H$_2$O, and brine, dried (MgSO$_4$), and concentrated. Purification by flash chromatography (1:1 EtOAc / hexane) gave 2.00 g (88%) of product as a white foam; $^1$H NMR (DMSO-d6) δ 2.00 (m, 21 H), 2.20 (s, 3 H), 4.00 (m, 4 H), 4.19 (m, 2 H), 4.40 (dd, 1 H), 4.56 (d, 1 H), 4.75 (m, 2 H), 4.80 (m, 1 H), 4.85 (d, 1 H), 5.05 (t, 1 H), 5.20 (t, 1 H), 5.30 (m, 2 H), 7.10 (d, 1 H), 7.25 (s, 1 H), 7.28 (d, 1 H), 7.84 (m, 1 H), 8.42 (d, 1 H), 8.45 (dd, 1 H), 8.80 (s, 1 H), 10.28 (s, 1 H). Anal. Calcd. for C$_{41}$H$_{48}$N$_2$O$_{21}$: C, 54.42; N, 5.35; N, 3.10. Found: C, 54.30; H, 5.27; N, 3.10.

EXAMPLE 5

N-[15-(Hegta-O-acetyl-β-D-maltosyloxymethyl)-2-methylphenyl]-3-aminobenzamide

A solution of N-[5-(hepta-O-acetyl-β-D-maltosyloxymethyl)-2-methylphenyl]-3-nitrobenzamide (0.55 g, 0.608 mmol), prepared as described in Example 4, in EtOAc (10 mL) was hydrogenated at atmospheric pressure over 10% Pd/C (0.20 g) for 2 h. The mixture was filtered and the filtrate was concentrated. Purification by flash chromatography (50% EtOAc/hexane) and trituration with ether/hexane gave 0.30 g (56%) of product as a white solid, mp 116–118° C.

EXAMPLE 6

3-Acetylamino-N-[5-(hepta-O-acetyl-β-D-maltosyloxymethyli)-2-methylphenyl]benzamide To a mixture of 3-amino-N-[2-methyl-5-(2,3,4,6-tetra-O-acetyl-β-D-glucopyranosyloxymethyl)phenyl]benzamide (0.85 g, 0.95 mmol), prepared as described in Example 5, and pyridine (0.10 g, 1.15 mmol) in THF (10 mL) was added acetyl chloride (0.10 g, 1.15 mmol). After 2 h, the mixture was concentrated, suspended in water, and filtered to give a white solid. Recrystallization from EtOAc/hexane gave 0.60 g (71%) of product as a white solid, mp 130–132° C.; $^1$H NMR (DMSO-$d_6$) δ 1.92 (s, 6 H), 1.94 (s, 3 H), 1.97 (s, 3 H), 2.05 (s, 9 H), 2.21 (s, 3 H), 4.00 (m, 4 H), 4.20 (m, 2 H), 4.40 (dd, J=12.2, 1.9 Hz, 1 H), 4.54 (d, J =12.2 Hz, 1 H), 4.73 (m, 2 H), 4.86 (dd, J=10.6, 3.7 Hz, 2 H), 4.97 (t, J=9.9 Hz 1 H), 5.21 (t, J=9.9 Hz, 1 H), 5.27 (t, J =9.9 Hz, 1 H), 5.29 (d, J=3.7 Hz, 1 H), 7.04 (d, J=7.9 Hz, 1 H), 7.06 (dd, J=7.9, 1.2 Hz, 1 H), 7.09 (s, 1 H), 7.44 (m, 1 H), 7.61 (d, J=7.9 Hz, 1 H), 7.82 (dd, J=8.5, 1.7 Hz, 1 H), 8.08 (m, 1 H), 9.84 (s, 1 H), 10.11 (s, 1 H). Anal. Calcd. for $C_{43}H_{52}N_2O_{20}$: C, 56.33; H, 5.72; N, 3.05. Found: C, 56.16; H, 5.79; N, 3.02.

EXAMPLE 7

N-{3-[2-(Hepta-O-acetyl-β-D-maltosyloxymethyl)-6-methylphenylcarbamoyl]phenyl}-3,5-di-tert-butyl-4-hydroxybenzamide The title compound was prepared according to the procedure of Example 4 as a white solid, mp 158–160° C.; $^1$H NMR (DMSO-$d_6$) δ 1.43 (s, 18 H), 1.94 (s, 3 H), 1.97 (s, 6 H), 1.98 (s, 6 H), 2.01 (s, 3 H), 2.08 (s, 3 H), 2.22 (s, 3 H), 4.00 (m, 4 H), 4.20 (m, 2 H), 4.39 (dd, J=12.0, 2.3 Hz, 1 H), 4.48 (d, J=12.4 Hz, 1 H), 4.69 (d, J=12.0 Hz, 1 H), 4.72 (t, J=12.4 Hz, 1 H), 4.82 (d, J=8.1 Hz, 1 H), 4.87 (dd,J=10.6, 3.9 Hz, 1 H), 4.98 (t, J=9.9 Hz, 1 H), 5.21 (t, J=9.9 Hz, 1 H), 5.28 (m, 2 H), 7.11 (dd, J=7.7, 1.4 Hz, 1 H), 7.22 (d, J=7.7 Hz, 1 H), 7.25 (s, 1 H), 7.49 (t, J=7.9 Hz, 1 H), 7.53 (s, 1 H), 7.70 (m, 3 H), 8.00 (d, J=7.9 Hz, 1 H), 8.22 (s, 1 H), 9.89 (s, 1 H), 10.21 (s, 1 H). Anal. Calcd. for $C_{56}H_{70}N_2O_{21}$: C, 60.75; H, 6.37; N, 2.53. Found: C, 60.63; H, 6.40; N, 2.46.

EXAMPLE 8

N-[5-(Hepta-O-acetyl-β-D-maltosyloxymethyl)-2-methylhenyl]-3-cyanobenzamide

The title compound was prepared according to the procedure of Example 4 as a white solid, mp 116–118° C.; $^1$H NMR (DMSO-$d_6$) δ 1.91 (s, 3 H), 1.93 (s, 3 H), 1.94 (s, 3 H), 1.97 (s, 6 H), 2.01 (s, 3 H), 2.07 (s, 3 H), 2.22 (s, 3 H), 3.90 (m, 4 H), 4.19 (m, 2 H), 4.38 (dt, J=1.24, 11.4 Hz, 1 H), 4.55 (d, J=12.2 Hz, 1 H), 4.72 (m, 2 H), 4.84 (t, J=6.2 Hz, 1 H), 4.86 (d, J=8.3 Hz, 1 H), 4.95 (t, J=9.9 Hz, 1 H), 5.21 (t, J=9.9 Hz, 1 H), 5.26 (d, J=3.7 Hz, 1 H), 5.31 (t, J=9.9 Hz, 1 H), 7.09 (dd, J=7.7, 0.8 Hz, 1 H), 7.26 (d, J=0.8 Hz, 1 H), 7.28 (d, J=7.7 Hz, 1 H), 7.75 (m, 1 H), 8.06 (d, J=7.7 Hz, 1 H), 8.25 (d, J=7.9 Hz, 1 H), 8.38 (s, 1 H), 10.08 (s, 1 H). Anal. Calcd. for $C_{42}H_{48}N_2O_{19}$: C, 57.03; H, 5.47; N, 3.16. Found: C, 56.80; H, 5.45; N, 3.06.

EXAMPLE 9

N-[5-(Hepta-O-acetyl-D-D-maltosyloxymethyl)-2-methylihenyl]-5-nitroisophthalamic Acid Methyl Ester The title compound was prepared according to the procedure of Example 4 as a white solid, mp 110–112° C.; $^1$H NMR (DMSO-$d_6$) δ 1.94 (s, 3 H), 1.97 (s, 6 H), 1.98 (s, 6 H), 2.01 (s, 3 H), 2.08 (s, 3 H), 2.22 (s, 3 H), 4.00 (m, 7 H), 4.20 (M, 2 H), 4.39 (dd, J=12.0, 2.3 Hz, 1 H), 4.48 (d, J=12.4 Hz, 1 H), 4.82 (d, J=8.1 Hz, 1 H), 4.87 (dd, J=10.6, 3.9 Hz, 1 H), 4.98 (t, J=9.9 Hz, 1 H), 5.21 (t, J=9.9 Hz, 1 H), 5.28 (m, 2 H), 7.13 (dd, J=7.7, 1.4 Hz, 1 H), 7.26 (s, 1 H), 7.28 (d, J=7.7 Hz, 1 H), 8.79 (m, 1 H), 8.91 (m, 1 H), 9.03 (m, 1 H), 10.51 (s, 1 H). Anal. Calcd. for $C_{43}H_{50}N_2O_{23}$: C, 53.64; H, 5.23; N, 2.91. Found: C, 53.70; H, 5.16; N, 2.65.

EXAMPLE 10

N-[5-(Hepta-O-acetyl-β-D-maltosyloxymethyl)-2-methylphenyl]acetamide

To a mixture of 5-(hepta-O-acetyl-β-maltosyloxymethyl)-2-methylphenylaniine (2.00 g, 2.65 mmol), prepared as described in Example 3, and triethylamine (0.80 g, 7.94 mmol) in $CH_2Cl_2$ (20 mL) was added acetyl chloride dropwise. After 3 h, water was added and the layers were separated. The organic layer was washed with brine, dried ($MgSO_4$), and concentrated to give an off-white foam. Purification by flash chromatography (40% to 60% EtOAc/hexane) gave a white foam. Trituration with ether/hexane gave 1.79 g (85%) of product as a white solid, mp 90–92° C.; $^1$H NMR (DMSO-$d_6$) δ 1.92 (s, 3 H), 1.93 (s, 3 H), 1.94 (s, 3 H), 1.97 (s, 6 H), 2.01 (s, 3 H), 2.03 (s, 3 H), 2.09 (s, 3 H), 2.17 (s, 3 H), 4.00 (m, 4 H), 4.20 (m, 2 H), 4.39 (dd, J=11.4, 1.1 Hz, 1 H), 4.49 (d, J=12.0 Hz, 1 H), 4.68 (d, J=12.0 Hz, 1 H), 4.70 (t, J=9.8 Hz, 1 H), 4.82 (d, J=8.9 Hz, 1 H), 4.86 (dd, J 10.6, 3.9 Hz, 1 H), 4.98 (t, J=9.8 Hz, 1 H), 5.02 (t, J=9.8 Hz, 1 H), 5.26 (m, 2 H), 6.96 (d, J=7.9 Hz, 1 H), 7.16 (d, J=7.9 Hz, 1 H), 7.32 (s, 1 H), 9.26 (s, 1 H). Anal. Calcd. for $C_{36}H_{47}NO_{19}$: C, 54.20; H, 5.94; N, 1.76. Found: C, 54.26; H, 5.95; N, 1.96.

EXAMPLE 11

N-[5-(Hepta-O-acetyl-β-D-maltosyloxlmethyl)-2-methylphenyl]propionamide

The title compound was prepared according to the procedure of Example 10 as a white foam; $^1$H NMR (DMSO-$d_6$) δ 1.08 (t, J=7.5 Hz, 3 H), 1.92 (s, 3 H), 1.93 (s, 3 H), 1.94 (s, 3 H), 1.97 (s, 3 H), 1.98 (s, 3 H), 2.02 (s, 3 H), 2.09 (s, 3 H), 2.16 (s, 3 H), 2.32 (q, J=7.5 Hz, 2 H), 3.96 (m, 4 H), 4.18 (m, 2 H), 4.39 (dd, J=12.0, 1.9 Hz, 1 H), 4.49 (d, J=12.5 Hz, 1 H), 4.71 (m, 2 H), 4.83 (m, 2 H), 4.98 (t, J=9.8 Hz, 1 H), 5.21 (t, J=9.8 Hz, 1 H), 5.28 (m, 2 H), 6.97 (d, J=8.1 Hz, 1 H), 7.17 (d, J=8.1 Hz, 1 H), 7.31 (s, 1 H), 9.19 (s, 1 H). Anal. Calcd. for $C_{37}H_{49}NO_{19}$: C, 54.74; H, 6.08; N, 1.72. Found: C, 54.38; H, 6.06; N, 1.74.

EXAMPLE 12

Pentanoic Acid N-[5-(Hepta-O-acetyl-β-D-maltosyloxymethyl)-2-methylphenyl]amide

The title compound was prepared according to the procedure of Example 10 as a white foam; $^1$H NMR (DMSO-$d_6$) δ 0.90 (t, J=7.3 Hz, 3 H), 1.33 (m, 2 H), 1.57 (m, 2 H), 1.92 (s, 3 H), 1.93 (s, 3 H), 1.94 (s, 3 H), 1.97 (s, 3 H), 1.98 (s, 3 H), 2.02 (s, 3 H), 2.09 (s, 3 H), 2.16 (s, 3 H), 2.31 (t, J=7.3 Hz, 2 H), 3.94 (m, 4 H), 4.19 (m, 2 H), 4.39 (d, J=11.8 Hz, 1 H), 4.48 (d, J=12.0 Hz, 1 H), 4.70 (m, 2 H), 4.85 (m, 2 H), 4.98 (t, J=9.8 Hz, 1 H), 5.21 (t, J=9.8 Hz, 1 H), 5.28 (m, 2 H), 6.97 (d, J=7.9 Hz, 1 H), 7.17 (d, J=7.9 Hz, 1 H), 7.29 (s, 1 H), 9.21 (s, 1 H). Anal. Calcd. for $C_{39}H_{53}NO_{19}$: C, 55.76; H, 6.36; N, 1.67. Found: C, 55.72; H, 6.39; N, 1.60.

EXAMPLE 13

N-[5-(Hepta-O-acetyl-β-D-maltosyloxymethyl)-2-methylphenyl]-2,2-dimethylpropionamide The title compound was prepared according to the procedure of Example 10 as a white foam; $^1$H NMR (DMSO-d$_6$) δ 1.22 (s, 9 H), 1.93 (s, 3 H), 1.94 (s, 3 H), 1.95 (s, 3 H), 1.97 (s, 3 H), 1.98 (s, 3 H), 2.02 (s, 3 H), 2.09 (s, 3 H), 2.13 (s, 3 H), 3.97 (m, 4 H), 4.18 (m, 2 H), 4.39 (m, 1 H), 4.51 (d, J=12.0 Hz, 1 H), 4.70 (m, 2 H), 4.84 (m, 2 H), 4.98 (t, J=9.8 Hz, 1 H), 5.21 (t, J=9.8 Hz, 1 H), 5.28 (m, 2 H), 7.02 (dd, J=7.9, 1.2 Hz, 1 H), 7.09 (d, J=1.2 Hz, 1 H), 7.19 (d, J=7.9 Hz, 1 H), 8.88 (s, 1 H). Anal. Calcd. for C$_{39}$H$_{53}$NO$_{19}$: C, 55.76; H, 6.36; N, 1.67. Found: C, 55.53; H, 6.56; N, 1.61.

EXAMPLE 14

Cycloprolanecarboxylic Acid N-[5-(Hepta-O-acetyl-β-D-maltosyloxymethyl)-2-methylphenyl]amide The title compound was prepared according to the procedure of Example 10 as a white foam; $^1$H NMR (DMSO-d$_6$) δ 0.76 (d, J=6.0 Hz, 4 H), 1.86 (m, 1 H), 1.92 (s, 3 H), 1.94 (s, 3 H), 1.96 (s, 6 H), 1.97 (s, 6 H), 2.01 (s, 3 H), 2.08 (s, 3 H), 2.18 (s, 3 H), 4.00 (m, 4 H), 4.21 (m, 2 H), 4.39 (dd, J=12.0, 2.3 Hz, 1 H), 4.48 (d, J=12.4 Hz, 1 H), 4.67 (d, J=12.0 Hz, 1 H), 4.71 (t, J=9.9 Hz, 1 H), 4.82 (d, J=8.1 Hz, 1 H), 4.86 (dd, J=10.6, 3.4 Hz, 1 H), 4.98 (t, J=9.9 Hz, 1 H), 5.21 (t, J=9.9 Hz, 1 H), 5.28 (m, 2 H), 6.96 (dd, J=7.7, 1.4 Hz, 1 H), 7.17 (d, J=7.7 Hz, 1 H), 7.28 (d, J=1.4 Hz, 1 H), 9.16 (s, 1 H). Anal. Calcd. for C$_{38}$H$_{49}$NO$_{19}$: C, 55.40; H, 6.00; N, 1.70. Found: C, 55.25; H, 5.99; N, 1.68.

EXAMPLE 15

Cyclopentanecarboxylic Acid N-[5-(Hegta-O-acetvy-β-D-maltosyloxymethyl)-2-methylphenyl] amide The title compound was prepared according to the procedure of Example 10 as a white foam; $^1$H NMR (DMSO-d$_6$) δ 1.58 (m, 2 H), 1.71 (m, 4 H), 1.85 (m, 2 H), 1.92 (s, 3 H), 1.93 (s, 3 H), 1.94 (s, 3 H), 1.97 (s, 6 H), 2.01 (s, 3 H), 2.08 (s, 3 H), 2.15 (s, 3 H), 2.82 (m, 1 H), 4.00 (m, 4 H), 4.21 (m, 2 H), 4.39 (dd, J=12.0, 2.3 Hz, 1 H), 4.48 (d, J=9.9 Hz, 1 H), 4.82 (d, J=8.1 Hz, 1 H), 4.86 (dd, J =10.6, 3.9 Hz, 1 H), 4.98 (t, J=9.9 Hz, 1 H), 5.21 (t, J=9.9 Hz, 1 H), 5.28 (m, 2 H), 6.96 (dd, J=7.7, 1.4 Hz, 1 H), 7.17 (d, J=7.7 Hz, 1 H), 7.28 (d, J=1.4 Hz, 1 H), 9.16 (s, 1 H). Anal. Calcd. for C$_{40}$H$_{53}$NO$_{19}$: C, 56.33; H, 5.72; N, 3.05. Found: C, 56.16; H, 5.79; N, 3.02.

EXAMPLE 16

N-[5-(Hepta-O-acetyl-β-D-maltosyloxymethyl)-2-methylphenyl]-3-cyclopentylpropionamide The title compound was prepared according to the procedure of Example 10 as a white foam; $^1$H NMR (DMSO-d$_6$) δ 1.10 (m, 2 H), 1.48 (m, 2 H), 1.60 (m, 4 H), 1.78 (m, 2 H), 1.92 (s, 6 H), 1.94 (s, 3 H), 1.95 (m, 1 H), 1.98 (s, 6 H), 2.01 (s, 3 H), 2.10 (s, 3 H), 2.18 (s, 3 H), 2.32 (t, J=7.7 Hz, 2 H), 4.00 (m, 4 H), 4.21 (m, 2 H), 4.39 (dd, J=12.0, 2.3 Hz, 1 H), 4.48 (d, J=12.4 Hz, 1 H), 4.67 (d, J=12.0 Hz, 1 H), 4.71 (t, J=9.9 Hz, 1 H), 5.28 (m, 2 H), 6.96 (dd, J=7.7, 1.4 Hz, 1 H), 7.17 (d, J=7.7 Hz, 1 H), 7.28 (d, J=1.4 Hz, 1 H), 9.21 (s, 1 H). Anal. Calcd. for C$_{42}$H$_{57}$NO$_{19}$: C, 57.33; H, 6.53; N, 1.59. Found: C, 57.50; H, 6.52; N, 1.80.

EXAMPLE 17

N-[5-(Hepta-O-acetyl-β-D-maltosyloxymethyl)-2-methyylhenyl]-4-(methanesulfonylamino)benzenesulfonamide To a mixture of 5-(hepta-O-acetyl-β-maltosyloxymethyl)-2-methylphenylamine (0.80 g, 1.06 mmol), prepared as described in Example 3, and pyridine (0.09 g, 1.06 rnmol) in THF (10 mL) was added 4-(methanesulfonylamino)benzenesulfonyl chloride (0.29 g, 1.06 mmol). After 18 h, the mixture was diluted with EtOAc, washed with 5% aqueous KHSO$_4$, saturated aqueous NaHCO$_3$, and brine, dried (MgSO$_4$), and concentrated. Purification by flash chromatography (2% MeOH/CH$_2$Cl$_2$) gave a white foam and trituration with ether gave 0.80 g (83%) of product as a white solid, mp 116°–118° C.; $^1$H NMR (DMSO-d$_6$) δ 1.94 (s, 6 H), 1.97 (s, 12 H), 2.01 (s, 3 H), 2.09 (s, 3 H), 3.08 (s, 3 H), 4.01 (m, 4 H), 4.19 (m, 2 H), 4.37 (d, J=12.2 Hz, 1 H), 4.41 (d, J=12.2 Hz, 1 H), 4.70 (m, 2 H), 4.80 (d, J=8.1 Hz, 1 H), 4.86 (dd, J=10.6, 3.7 Hz, 1 H), 4.98 (t, J=9.9 Hz), 1 H, 5.21 (t, J=9.9 Hz, 1 H), 5.27 (t, J=9.9 Hz, 1 H), 5.29 (d, J=3.7 Hz, 1 H), 7.00 (dd, J=7.9, 1.2 Hz, 1 H), 7.04 (d, J=1.2 Hz, 1 H), 7.09 (d, J=7.9 Hz, I H), 7.27 (d, J=8.7 Hz, 2 H), 7.55 (d, J=8.7 Hz, 2 H), 9.50 (s, 1 H), 10.35 (s, 1 H). Anal. Calcd. for C$_{41}$H$_{52}$N$_2$O$_{22}$S$_2$: C, 49.79; H, 5.30; N, 2.83. Found: C, 49.50; H, 5.28; N, 2.93.

EXAMPLE 18

N-[5-(Hepta-O-acetyl-β-D-maltosyloxlmethyl)-2-methylphenyl]-4-cyanobenzenesulfonamide The title compound was prepared according to the procedure of Example 17 as a white foam; $^1$H NMR (DMSO-d$_6$) δ 1.88 (s, 3 H), 1.93 (s, 3 H), 1.94 (s, 3 H), 1.95 (s, 3 H), 1.97 (s, 3 H), 1.98 (s, 3 H), 2.02 (s, 3 H), 2.09 (s, 3 H), 3.96 (m, 4 H), 4.35 (m, 2 H), 4.38 (d, J=10.6 Hz, 1 H), 4.46 (d, J=12.2 Hz, 1 H), 4.66 (m, 2 H), 4.81 (d, J=7.9 Hz, 1 H), 4.86 (dd, J=10.4, 3.7 Hz, 1 H), 4.98 (t, J=9.8 Hz, 1 H), 5.22 (t, J=10.4 Hz, 1 H), 5.29 (m, 2 H), 6.97 (d, J=1.5 Hz, 1 H), 7.03 (dd, J=7.9, 1.5 Hz, 1 H), 7.12 (d, J=7.9 Hz, I H), 7.77 (d, J=8.7 Hz, 2 H), 8.03 (d, J=8.7 Hz, 2 H), 9.94 (s, 1 H). Anal. Calcd. for C$_{41}$H$_{48}$N$_2$O$_{20}$S: C, 53.48; H, 5.25; N, 3.04. Found: C, 53.08; H, 5.21; N, 2.89.

EXAMPLE 19

N-[5-(Hepta-O-acetyl-β-D-maltosyloxymethyl)-2-methylphenyl]-4-trifluoromethylbenzenesulfonamide The title compound was prepared according to the procedure of Example 17 as a white foam; $^1$H NMR (DMSO-d$_6$) δ 1.86 (s, 3 H), 1.93 (s, 3 H), 1.94 (s, 3 H), 1.95 (s, 3 H), 1.97 (s, 3 H), 1.98 (s, 3 H), 2.02 (s, 3 H), 2.08 (s, 3 H), 3.95 (m, 4 H), 4.18 (m, 2 H), 4.38 (m, 1 H), 4.45 (d, J=12.7 Hz, 1 H), 4.65 (m, 2 H), 4.80 (d, J=7.9 Hz, 1 H), 4.86 (dd, J=10.6, 3.9 Hz, 1 H), 4.98 (t, J=9.8 Hz, 1 H), 5.21 (t, J=9.8 Hz, 1 H), 5.28 (m, 2 H), 7.00 (s, 1 H), 7.03 (d, J=7.9 Hz, 1 H), 7.12 (d, J=7.9 Hz, 1 H), 7.83 (d, J=8.1 Hz, 2 H), 7.95 (d, J=8.1 Hz, 2 H), 9.90 (s, 1 H). Anal. Calcd. for C$_{41}$H$_{48}$F$_3$NO$_{20}$S: C, 51.09; H, 5.02; N, 1.45. Found: C, 50.87; H, 4.99; N, 1.50.

EXAMPLE 20

N-[5-(Hepta-O-acetyl-β-D-maltosylioxymethyl)-2-methylphenyl]-3-trifluoromethylbenzenesulfonamide The title compound was prepared according to the procedure of Example 17 as a white foam; $^1$H NMR (DMSO-d6) δ 1.86 (s, 3 H), 1.93 (s, 3 H), 1.94 (s, 3 H), 1.95 (s, 3 H), 1.97 (s, 3 H), 1.98 (s, 3 H), 2.02 (s, 3 H), 2.08 (s, 3 H), 3.95 (m, 4 H), 4.18 (m, 2 H), 4.36 (m, 1 H), 4.44 (d, J=12.7 Hz, 1 H), 4.64 (d, J=12.7 Hz, 1 H), 4.69 (dd, J=9.5, 8.1 Hz, 1 H), 4.79 (d, J=8.5 Hz, 1 H), 4.86 (dd, J=10.6, 3.7 Hz, 1 H), 4.98 (t, J=9.8 Hz, 1 H), 5.22 (dd, J=10.4, 9.5 Hz, 1 H), 5.28 (m, 2 H), 6.96 (d, J=1.5 Hz, l H), 7.04 (dd, J =8.1, 1.5 Hz, 1 H), 7.12 (d, J=8.1 Hz, 1 H), 7.81 (m, 1 H), 7.86 (s, l H), 7.90 (d, J=8.5 Hz, 1 H), 8.05 (d, J=7.9 Hz, 1 H), 9.86 (s, 1 H). Anal. Calcd. for $C_{41}H_{48}F_3NO_{20}S$: C, 51.09; H, 5.02; N, 1.45. Found: C, 50.87; H, 4.97; N, 1.46.

EXAMPLE 21

N-[5-(Hepta-O-acetyl-β-D-maltosyloxymethyl)-2-methylphenyl]-2-trifluoromethylbenzenesulfonamide The title compound was prepared according to the procedure of Example 17 as a white foam; $^1$H NMR (DMSO-$d_6$) δ 1.90 (s, 3 H), 1.92 (s, 3 H), 1.93 (s, 3 H), 1.94 (s, 3 H), 1.98 (s, 6 H), 2.02 (s, 3 H), 2.08 (s, 3 H), 3.95 (m, 4 H), 4.18 (m, 2 H), 4.38 (m, 1 H), 4.44 (d, J=12.2 Hz, 1 H), 4.63 (d, J=12.2 Hz, 1 H), 4.69 (dd, J=9.5, 8.1 Hz, 1 H), 4.77 (d, J=8.1 Hz, 1 H), 4.86 (dd, J=10.6, 3.9 Hz, 1 H), 4.98 (t, J=9.5 Hz, 1 H), 5.22 (dd, J=10.4, 9.8 Hz, 1 H), 5.28 (m, 2 H), 7.02 (m, 2 H), 7.11 (d, J=7.9 Hz, 1 H), 7.80 (m, 3 H), 7.99 (d, J=7.5 Hz, 1 H), 9.79 (s, 1 H). Anal. Calcd. for $C_{41}H_{48}F_3NO_{20}S$: C, 51.09; H, 5.02; N, 1.45. Found: C, 50.85; H, 4.89; N, 1.45.

EXAMPLE 22

N-[5-(Hepta-O-acetyl-β-D-maltosyloxymethyl)-2-methylphenyl]-3-(methanesulfonylamino)benzenesulfonamide The title compound was prepared according to the procedure of Example 17 as a white solid, mp 122°–124° C.; $^1$H NMR (DMSO-$d_6$) δ 1.84 (s, 3 H), 1.93 (s, 3 H), 1.94 (s, 6 H), 2.01 (s, 3 H), 2.09 (s, 3 H), 2.93 (s, 3 H), 4.00 (m, 4 H), 4.20 (m, 2 H), 4.40 (d, J=12.0 Hz, 1 H), 4.43 (d, J=12.4 Hz, 1 H), 4.70 (m, 2 H), 4.79 (d, J=7.9 Hz, 1 H), 4.86 (dd, J=10.6, 3.9 Hz, 1 H), 4.97 (t, J=9.9 Hz, 1 H), 5.21 J=9.9 Hz, 1 H), 5.27 (d, J=3.9 Hz, l H), 5.29 (t, J=9.9 Hz, 1 H), 7.01 (d, J=7.7 Hz, 1 H), 7.02 (s, 1 H), 7.09 (d, J=7.7 Hz, 1 H), 7.28 (dd, J=7.9, 1.9 Hz, 1 H), 7.40 (dd, J=7.9, 1.9 Hz, 1 H), 7.47 (m, 1 H), 7.53 (m, 1 H), 9.66 (s, 1 H), 10.11 (s, 1 H). Anal. Calcd. for $C_{41}H_{52}N_2O_{22}S_2$: C, 49.79; H, 5.30; N, 2.83. Found: C, 49.36; H, 5.31; N, 2.95.

EXAMPLE 23

N-[5-(Hepta-O-acetyl-β-D-maltosyloxymethyl)-2-methylphenyl]-4-methoxybenzenesulfonamide The title compound was prepared according to the procedure of Example 17 as a white foam; $^1$H NMR (DMSO-$d_6$) δ 1.90 (s, 3 H), 1.93 (s, 3 H), 1.94 (s, 3 H), 1.95 (s, 3 H), 1.98 (s, 3 H), 2.02 (s, 3 H), 2.09 (s, 3 H), 3.81 (s, 3 H), 3.96 (m, 4 H), 4.18 (m, 2 H), 4.38 (m, 1 H), 4.44 (d, J=12.5 Hz, 1 H), 4.63 (d, J=12.5 Hz, 1 H), 4.70 (dd, J=9.3, 8.1 Hz, 1 H), 4.77 (d, J=7.9 Hz, 1 H), 4.86 (dd, J=10.6, 3.9 Hz, 1 H), 4.98 (t, J=9.8 Hz, 1 H), 5.22 (dd, J=10.4, 9.8 Hz, 1 H), 5.28 (m, 2 H), 7.03 (m, 5 H), 7.55 (d, J=9.1 Hz, 1 H), 9.41 (s, 1 H). Anal. Calcd. for $C_{41}H_{51}NO_{21}S$: C, 53.19; H, 5.55; N, 1.51. Found: C, 52.80; H, 5.41; N, 1.52.

EXAMPLE 24

N-[5-(Hepta-O-acetyl-β-D-maltosyloxymethyl)-2-methlhenyl]-4-methylbenzenesulfonamide The title compound was prepared according to the procedure of Example 17 as a white foam; $^1$H NMR (DMSO-$d_6$) δ 1.87 (s, 3 H), 1.94 (s, 6 H), 1.95 (s, 3 H), 1.98 (s, 6 H), 2.02 (s, 3 H), 2.09 (s, 3 H), 2.36 (s, 3 H), 3.95 (m, 4 H), 4.17 (m, 2 H), 4.38 (dd, J=11.8, 1.0 Hz, 1 H), 4.43 (d, J=12.2 Hz, 1 H), 4.64 (d, J=12.2 Hz, 1 H), 4.70 (dd, J=9.3, 8.1 Hz, 1 H), 4.77 (d, J=8.1 Hz, 1 H), 4.86 (dd, J=10.4, 3.7 Hz, 1 H), 4.98 (t, J=9.8 Hz, 1 H), 5.22 (t, J=10.1 Hz, 1 H), 5.28 (m, 2 H), 6.98 (d, J=8.1 Hz, 1 H), 7.03 (s, 1 H), 7.08 (d, J=8.1 Hz, 1 H), 7.33 (d, J=8.1 Hz, 2 H), 7.51 (d, J=8.1 Hz, 2 H), 9.49 (s, 1 H). Anal. Calcd. for $C_{41}H_{51}NO_{20}S$: C, 54.12; H, 5.65; N, 1.54. Found: C, 53.79; H, 5.53; N, 1.53.

EXAMPLE 25

N-[5-(Hepta-O-acetyl-β-D-maltosyloxymethyl)-2-methylphenyl]-4-chlorobenzenesulfonamide The title compound was prepared according to the procedure of Example 17 as a white foam; $^1$H NMR (DMSO-$d_6$) δ 1.89 (s, 3 H), 1.94 (s, 6 H), 1.95 (s, 3 H), 1.98 (s, 6 H), 2.02 (s, 3 H), 2.09 (s, 3 H), 3.99 (m, 4 H), 4.16 (dd, J=12.0, 4.4 Hz, 1 H), 4.20 (m, 1 H), 4.39 (dd, J=11.4, 0.6 Hz, 1 H), 4.45 (d, J=12.2 Hz, 1 H), 4.65 (d, J=12.2 Hz, 1 H), 4.71 (dd, J=9.3, 7.9 Hz, 1 H), 4.79 (d, J=7.9 Hz, 1 H), 4.86 (dd, J=10.4, 3.7 Hz, 1 H), 4.98 (t, J=9.8 Hz, 1 H), 5.22 (dd, J=10.2, 9.5 Hz, 1 H), 5.28 (m, 2 H), 7.01 (m, 2 H), 7.11 (d, J=7.7 Hz, 1 H), 7.62 (s, 4 H), 9.72 (s, 1 H). Anal. Calcd. for $C_{40}H_{48}ClNO_{20}S$: C, 51.64; H, 5.20; N, 1.51. Found: C, 51.47; H, 5.10; N, 1.58.

EXAMPLE 26

N-[5-(Hepta-O-acetyl-β-D-maltosyloxymethyl)-2-methylphenyl]-4-chloro-3-nitrobenzeneslulfonamide The title compound was prepared according to the procedure of Example 17 as a white foam; $^1$H NMR (DMSO-$d_6$) δ 1.92 (s, 3 H), 1.93 (s, 3 H), 1.94 (s, 3 H), 1.97 (s, 6 H), 1.98 (s, 3 H), 2.01 (s, 3 H), 2.07 (s, 3 H), 4.00 (m, 4 H), 4.20 (m, 2 H), 4.39 (dd, J=12.0, 2.3 Hz, l H), 4.46 (d, J=12.0 Hz, 1 H), 4.68 (m, 2 H), 4.80 (d, J=8.1 Hz, 1 H), 4.85 (dd, J=10.6, 3.7 Hz, 1 H), 4.98 (t, J=9.9 Hz, 1 H), 5.22 (t, J=9.9 Hz, 1 H), 5.28 (d, J=3.7 Hz, 1 H), 5.30 (m, 1 H), 6.94 (d, J=1.5 Hz, 1 H), 7.07 (dd, J=7.7 1.5 Hz, 1 H), 7.17 (d, J=7.7 Hz, 1 H), 7.86 (dd, J=8.5, 2.1 Hz, 1 H), 7.96 (d, J=8.5 Hz, 1 H), 8.29 (d, J=2.1 Hz, 1 H), 10.02 (s, 1 H). Anal. Calcd. for $C_{40}H_{47}ClN_2O_{22}S$: C, 49.26; H, 4.86; N, 2.87. Found: C, 49.19; H, 4.71; N, 2.62.

EXAMPLE 27

N-[5-(Hepta-O-acetyl-β-D-maltosyloxymethyl)-2-methylpheny]methanesulfonamide

The title compound was prepared according to the procedure of Example 17 as a white solid, mp 96°–98° C.; $^1$H NMR (DMSO-$d_6$) δ 1.93 (s, 6 H), 1.94 (s, 3 H), 1.97 (s, 6 H), 2.01 (s, 3 H), 2.08 (s, 3 H), 2.28 (s, 3 H), 2.96 (s, 3 H), 3.98 (m, 4 H), 4.19 (m, 2 H), 4.40 (dd, J=12.0, 2.3 Hz, 1 H), 4.71 (m, 2 H), 4.85 (m, 2 H), 4.97 (t, J=9.9 Hz, 1 H), 5.21 (t, J=9.9 Hz, 1 H), 5.27 (d, J=3.7 Hz, 1 H), 5.29 (t, J=9.9 Hz, 1 H), 7.05 (dd, J=7.7, 1.2 Hz, 1 H), 7.19 (d, J=1.2 Hz, 1 H), 7.22 (d, J=7.7 Hz, 1 H), 9.05 (s, 1 H). Anal. Calcd. for $C_{35}H_{47}NO_{20}S$: C, 50.42; H, 5.68; N, 1.68. Found; C, 50.29; H, 5.56; N, 1.58.

EXAMPLE 28

Butane-1-sulfonic Acid N-[5-(Hepta-O-acetyl-β-D-maltosyloxymethyl)-2-methylphenyl]amide The title compound was prepared according to the procedure of Example 17 as a white foam; $^1$H NMR (DMSO-$d_6$) δ 0.87 (t, J=7.5 Hz, 3 H), 1.39 (m, 2 H), 1.68 (m, 2 H), 1.93 (s, 3 H), 1.94 (s, 3 H), 1.95 (s, 3 H), 1.97 (s, 6 H), 1.98 (s, 3 H), 2.02 (s, 3 H), 2.09 (s, 3 H), 2.28 (s, 3 H), 3.05 (dd, J=7.7, 6.6 Hz, 2 H), 3.95 (m, 4 H), 4.18 (m, 2 H), 4.40 (dd, J=11.8, 1.2 Hz, 1 H), 4.51 (d, J=12.2 Hz, 1 H), 4.71 (m, 2 H), 4.85 (m, 2 H), 4.98 (t, J=9.8 Hz, 1 H), 5.21 (t, J=9.8 Hz, 1 H), 5.29 (m, 2 H), 7.03 (d, J=7.7 Hz, 1 H), 7.18 (s, 1 H), 7.21 (d, J=7.7 Hz, 1 H), 9.04 (s, 1 H). Anal. Calcd. for $C_{38}H_{51}NO_{20}S$: C, 52.23; H, 5.88; N, 1.60. Found: C, 51.88; H, 5.97; N, 1.52.

EXAMPLE 29

4-(Hepta-O-acetyl-δ-D-maltosyloxymethyl)-2-methylphenylamine Hydrochloride

Step 1

4-(Hepta-O-acetyl-β-maltosyloxymethyl)-2-methyl-1-nitrobenzene

A mixture of 3-methyl-4-nitrobenzyl alcohol (5.0 g, 0.030 mol), acetobromo-α-maltose (25.1 g, 0.036 mol), $Hg(CN)_2$ (9.2 g, 0.036 mol), and $HgBr_2$ (5.4 g, 0.015 mol) in THF (130 mL) was stirred at room temperature for 48 h. Saturated aqueous NaCl (100 mL) was added and the mixture was stirred for 20 min. The reaction mixture was extracted with EtOAc and the organic phase was washed with saturated aqueous $NaHCO_3$ and saturated aqueous NaCl, dried ($MgSO_4$), and concentrated to give a yellow foam. Trituration with ether gave 6.9 g (30%) of product as a white solid, mp 138°–140° C.; $^1$H NMR (DMSO-$d_6$) δ 1.92 (s, 6 H), 1.95 (s, 6 H), 1.99 (s, 6 H), 2.05 (s, 3 H), 2.48 (s, 3 H), 3.96 (m, 4 H), 4.15 (m, 2 H), 4.37 (d, J=11.7 Hz, 1 H), 4.81 (m, 6 H), 5.25 (m, 3 H), 7.30 (d, J=8.3 Hz, 1 H), 7.33 (s, 1 H), 7.98 (d, J=8.3 Hz, 1 H).

Step 2

4-(Hepta-O-acetyl-β-maltosyloxymethyl)-2-methylphenylamine Hydrochloride

A solution of of 4-(hepta-O-acetyl-β-maltosyloxymethyl)-2-methyl-1-nitrobenzene (5.95 g, 7.57 mmol) in EtOAc (80 mL) was hydrogenated at 50 psi over 10% Pd/C (2.60 g) for 30 min. The catalyst was removed by filtration and the filtrate was concentrated to give a white foam. Trituration with 40% EtOAc/hexane gave 5.70 g (100%) of product as a white solid, mp 164°–166° C.; $^1$H NMR (DMSO-d6) δ 1.92 (s, 3 H), 1.94 (s, 3 H), 1.97 (s, 6 H), 1.99 (s, 6 H), 2.01 (s, 3 H), 2.07 (s, 3 H), 3.98 (m, 4 H), 4.17 (m, 2 H), 4.30 (d, J=12.0 Hz, 1 H), 4.37 (d, J=12.0 Hz, 1 H), 4.50 (d, J=12.0 Hz, 1 H), 4.62 (d, J=10.6 Hz, 1 H), 4.75 (d, J=8.1 Hz, 1 H), 4.82 (m, 2 H), 4.97 (t, J=9.9 Hz, 1 H), 5.25 (m, 4 H), 6.58 (d, J=8.3 Hz, 1 H), 6.78 (d, J=8.3 Hz, 1 H), 6.81 (s, 1 H).

A hydrochloride salt was prepared by treating a solution of free base (0.50 g, 0.66 mmol) in dioxane (1.5 mL) with saturated ethereal HCl (25 mL). The precipitate was collected by filtration to give 0.35 g (67%) of the title compound as a white solid, mp 160° C. (dec). Anal. Calcd. for $C_{34}H_{46}NO_{18}\cdot HCl$: C, 51.55; H, 5.85; N, 1.77. Found: C, 50.92; H, 5.54; N, 1.84.

EXAMPLE 30

N-[4-(Hepta-O-acetyl-β-D-maltosyloxymethyl)-2-methylphenyl]-4-(methanesulfonylamino)benzenesulfonamide To a cooled (0° C.) solution of 4-(hepta-O-acetyl-β-maltosyloxymethyl)-2-methylphenylamine (0.80 g, 1.06 mmol), prepared as described in Example 29, and $Et_3N$ (0.11 g, 1.11 mmol) in THF (8 mL) was added 4-(methylsulfonylamino)benzenesulfonyl chloride (0.30 g, 1.11 mmol). The cooling bath was removed and stirring was continued for 24 h at room temperature. EtOAc was added and the mixture was washed with water and brine, dried ($MgSO_4$), and concentrated. Purification by flash chromatography (40% EtOAc/hexane) gave 0.50 g (48%) of product as a white solid, mp 116°–118° C.; $^1$H NMR (DMSO-$d_6$) δ 1.88 (s, 3 H), 1.92 (s, 3 H), 1.94 (s, 3 H), 1.97 (s, 9 H), 2.01 (s, 3 H), 2.07 (s, 3 H), 3.10 (s, 3 H), 3.98 (m, 4 H), 4.19 (m, 2 H), 4.37 (dd, J=12.0, 2.3 Hz, 1 H), 4.48 (d, J=12.4 Hz, 1 H), 4.82 (d, J=8.1 Hz, 1 H), 4.87 (dd, J=10.6, 3.9 Hz, 1 H), 4.98 (t, J=9.9 Hz, 1 H), 5.21 (t, J =9.9 Hz, 1 H), 5.25 (d, J =3.7 Hz, 1 H), 5.28 (t, J =9.9 Hz, 1 H), 6.93 (d, J=8.1 Hz, 1 H), 6.98 (dd, J=8.1, 1.4 Hz, 1 H), 7.03 (d, J=1.4 Hz, 1 H), 7.28 (d, J=8.9 Hz, 2 H), 7.61 (d, J=8.9 Hz, 2 H), 9.48 (s, 1 H), 10.36 (s, 1 H). Anal. Calcd. for $C_{41}H_{52}N_2O_{22}S_2$: C, 49.79; H, 5.30; N, 2.83. Found: C, 49.66; H, 5.44; N, 2.86.

EXAMPLE 31

N-[4-(Hepta-O-acetyl-β-D-maltosvioxymethyl)-2-methylnhenyl]-4-nitro-N-(4-nitrophenylsulfonyl)benzenesulfonamide The title compound was prepared according to the procedure of Example 30, Step 3 but di-4-nitrobenzensulfonation occured to give the product as a yellow solid, mp 126°–128° C.; $^1$H NMR (DMSO-$d_6$) δ 1.90 (s, 3 H), 1.94 (s, 3 H), 1.95 (s, 3 H), 1.97 (s, 3 H), 1.98 (s, 3 H), 2.02 (s, 3 H), 2.07 (s, 3 H), 2.08 (s, 3 H), 4.00 (m, 4 H), 4.20 (m, 2 H), 4.39 (dd, J=12.0, 2.3 Hz, 1 H), 4.67 (d, J=12.0 Hz, 1 H), 4.78 (m, 2 H), 4.85 (dd, J=10.6, 3.9 Hz, 1 H), 4.95 (d, J=8.1 Hz, 1 H), 5.01 (d, J=9.9 Hz, 1 H), 5.21 (t, J=9.9 Hz, 1 H), 5.30 (d, J=3.7 Hz, 1 H), 5.38 (t, J=9.9 Hz, 1 H), 6.95 (d, J=8.1 Hz, 1 H), 7.18 (dd, J=8.1, 1.4 Hz, 1 H), 7.28 (d, J=1.4 Hz, 1 H), 8.08 (d, J=8.9 Hz, 4 H), 8.52 (d, J=8.9 Hz, 4 H). Anal. Calcd. for $C_{46}H_{51}N_3O_{26}S_2$: C, 49.07; H, 4.57; N, 3.73. Found: C, 48.77; H, 4.59; N, 3.5.

EXAMPLE 32

N-Acetyl-4-[acetyl(methanesulfonyl)amino]-N-[5-(', 6'-O-isopropylidine-2,2',3,3',6-penta-O-acetyl-β-D-maltosylloxymethyl)-2-methylphenyl]benzenesulfonamide

Step 1

N-[5-(β-D-Maltosyloxymethyl)-2-methylphenyl]-4-(methanesulfonylamino)benzenesulfonamide A mixture of N-[5-(hepta-O-acetyl-β-D-maltosyloxymethyl)-2-methylphenyl]-4-(methanesulfonylamino)benzenesulfonamide (2.08 g, 2.10 mmol), prepared as described in Example 17, and 25 weight % NaOMe in MeOH (4.82 mL, 21.0 mmol) in MeOH (20 mL) was stirred at room temperature for 2 h. Amberlite IR-120($H^+$) was added until a pH of 5–6 resulted. The mixture was filtered and the filtrate was concentrated to give 1.50 g (98%) of product as an off-white foam. The material was used directly in the next reaction without further purification.

Step 2

N-Acetyl -4-[acetyl (methanesulfonyl)amino]-N-[5-(4',6'-O-isopropylidine-2,2',3,3',6-penta-O-acetyl-β-D-maltosyloxymethyl)-2-methylphenyl]benzenesulfonamide To a suspension of N-[5-(β-D-maltosyloxymethyl)-2-methylphenyl]-4-(methanesulfonylamino)

benzenesulfonamide (0.79 g, 1. 14 mmol) in CH$_3$CN (20 mL) was added dimethoxypropane (0.36 g, 3.41 mmol) and camphorsulfonic acid (13 mg, 0.06 mmol). After 6 h, the mixture was concentrated, taken up in CH$_3$CN (20 mL), and dimethoxypropane (0.85 g, 8.13 mmol) was added. After 2.5 days, saturated aqueous NaHCO$_3$ (3 mL) was added and the mixture was filtered. The filtrate was concentrated, taken up in acetone, passed through a short plug of silica gel, and concentrated to give 0.83 g (100%) of N-[5-(4',6'-O-isopropylidine-β-D-maltosyloxymethyl)-2-methylphenyl]-4-(methanesulfonylamino)benzenesulfonamide as a brown foam. This material was used directly in the next reaction without further purification.

To a cooled (0° C.) solution of N-[5-(4',6'-O-isopropylidine-β-D-maltosyloxymethyl)-2-methylphenyl]-4-(methanesulfonylamino)benzenesulfonamide (0.83 g, 1.14 mmol) in pyridine (2.3 mL) was added acetic anhydride (2.2 mL). The cooling bath was removed and stirring was continued at room temperature for 2 days. The mixture was recooled (0° C.) and ice was added. After 30 min, the mixture was concentrated, taken up in EtOAc, washed with 0.5N HCl, water, and saturated aqueous NaHCO$_3$, dried (MgSO$_4$), and concentrated. Purification by flash chromatography (60% EtOAc/hexane) and trituration with ether gave 0.52 g (44%) of product as an off-white solid, mp 159°–163° C.; mass spectrum m/z [M+H]$^+$1029. Anal. Calcd. for C$_{44}$H$_{56}$N$_2$O$_{22}$S$_2$: C, 51.36; H, 5.49; N, 2.72. Found: C, 51.10; H, 5.53; N, 2.72.

EXAMPLE 33

N-Propionyl-4-[prolpionyl](methanesulfonyl)amino]-N-[5-(hepta-O-propionyl-β-D-maltosyloxymethyl)-2-methiylphenyl]benzenesulfonamide A mixture of N-[5-(β-D-maltosyloxymethyl)-2-methylphenyl]-4-(methanesulfonylamino)benzenesulfonamide (0.195 g, 0.281 mmol), prepared according to Example 32, Step 1, pyridine (0.90 g, 11.23 mmol), and propionic anhydride (1.50 g, 11.23 mmol) was stirred at room temperature for 3 days. The mixture was concentrated, diluted with EtOAc, washed with water, 10% KHSO$_4$, saturated aqueous NaHCO$_3$, and brine, dried (MgSO$_4$), and concentrated to give a yellow foam. Trituration with hexane gave 0.11 g (33%) of product as a white solid, mp 98°–100° C.; $^1$H NMR (DMSO-d$_6$) δ 1.00 (m, 21 H), 2.20 (m, 17 H), 3.60 (s, 3 H), 4.00 (m, 4 H), 4.20 (m, 2 H), 4.40 (m, 1 H), 4.62 (m, 1 H), 4.80 (m, 2 H), 4.88 (dd, J=12.0, 2.3 Hz, 1 H), 4.97 (t, J=9.9 Hz, 1 H), 5.02 (t, J=9.9 Hz, 1 H), 5.26 (m, 2 H), 5.36 (m, 1 H), 7.21 (m, 1 H), 7.34 (m, 1 H), 7.45 (m, 1 H), 7.80 (m, 2 H), 8.13 (m, 2 H). Anal. Calcd. for C$_{54}$H$_{74}$N$_2$O$_{24}$S$_2$: C, 54.09; H, 6.22; N, 2.34. Found: C, 53.93; H, 6.11; N, 2.40.

We claim:
1. A compound of the general formula I

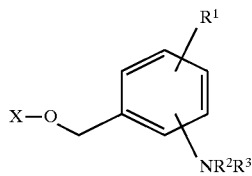

where X is

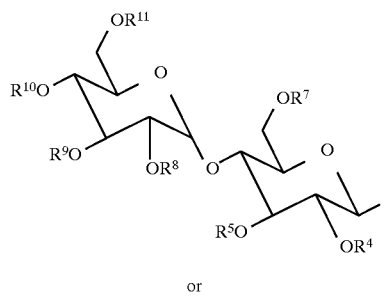

or

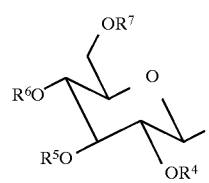

R$^1$ is H, alkyl having 1 to 6 carbon atoms, halo, CF$_3$, CN, NO$_2$, or alkoxy having 1 to 6 carbon atoms;

R$^2$ is H, an acyl group having 1 to 6 carbon atoms, phenylsulfonyl, or phenylsulfonyl substituted with NO$_2$; and R$^3$ is H, an acyl group having 1 to 8 carbon atoms, alkylsulfonyl having 1 to 6 carbon atoms, benzoyl, benzoyl substituted with NH$_2$, NO$_2$, CN, C$_1$–C$_6$ alkyl, C$_1$–C$_6$ alkoxy, C$_2$–C$_{15}$ acylamino, CF$_3$, C$_1$–C$_6$ alkanesulfonylamino, acetyl(methanesulfonyl)amino, halo, or OH, phenylsulfonyl, or phenylsulfonyl substituted with C$_1$–C$_6$ alkyl, C$_1$–C$_6$ alkoxy, C$_2$–C$_{15}$ acylamino, NO$_2$, CN, CF$_3$, C$_1$–C$_6$ alkanesulfonylamino, acetyl(methanesulfonyl)amino, OH, or halo;

R$^4$, R$^5$, R$^6$, R$^7$, R$^8$, and R$^9$ are each, independently, an acyl group having 1 to 6 carbon atoms; and R$^{10}$ and R$^{11}$ are each, independently, an acyl group having 1 to 6 carbon atoms, or the R$^{10}$ and R$^{11}$ groups on the 4' and 6' positions of the maltose or the 4 and 6 positions of the glucose form an isopropylidene group; or a pharmaceutically acceptable salt thereof.

2. A compound according to claim 1 of formula I

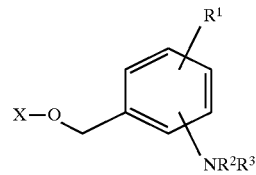

where X is

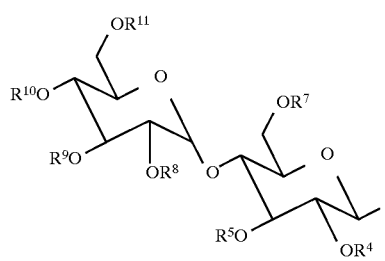

-continued or

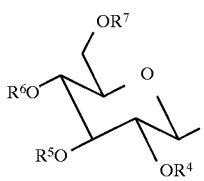

R¹ is H or alkyl having 1 to 6 carbon atoms;

R² is H, an acyl group having 1 to 6 carbon atoms, phenylsulfonyl, or 4-nitrophenylsulfonyl; and R³ is an acyl group having 1 to 8 carbon atoms, benzoyl, benzoyl substituted with a nitro, amino, acetamido, 3,5-di-tert-butyl-4-hydroxybenzamido, cyano, or carbomethoxy group, alkylsulfonyl having 1 to 6 carbon atoms, phenylsulfonyl, or phenylsulfonyl substituted with a methanesulfonylamino, cyano, trifluoromethyl, alkoxy having 1 to 6 carbon atoms, alkyl having 1 to 6 carbon atoms, chloro, or nitro group;

R⁴, R⁵, R⁶, R⁷, R⁸, and R⁹ are each, independently, an acyl group having 1 to 6 carbon atoms; and R¹⁰ and R¹¹ are each, independently, an acyl group having 1 to 6 carbon atoms, or the R² groups on the 4' and 6' positions of the maltose or the 4 and 6 positions of the glucose form an isopropylidene group;

or a pharmaceutically acceptable salt thereof.

3. A compound of claim 1 which is N-[2-methyl-5-(2,3,4,6-tetra-O-acetyl-β-D-glucopyranosyloxymethyl)phenyl]-3-nitrobenzamide or a pharmaceutically acceptable salt thereof.

4. A compound of claim 1 which is 3-amino-N-[2-methyl-5-(2,3,4,6-tetra-O-acetyl-β-D-glucopyranosyloxymethyl) phenyl]benzamide hydrate or a pharmaceutically acceptable salt thereof.

5. A compound of claim 1 which is 5-(hepta-O-acetyl-β-maltosyloxymethyl)-2-methylphenylamine hydrochloride or a pharmaceutically acceptable salt thereof.

6. A compound of claim 1 which is N-[5-(hepta-O-acetyl-β-D-maltosyloxymethyl)-2-methylphenyl]-3-nitrobenzamide or a pharmaceutically acceptable salt thereof.

7. A compound of claim 1 which is N-[5-(hepta-O-acetyl-β-D-maltosyloxymethyl)-2-methylphenyl]-3-aminobenzamide or a pharmaceutically acceptable salt thereof.

8. A compound of claim 1 which is 3-acetylamino-N-[5-(hepta-O-acetyl-β-D-maltosyloxymethyl)-2-methylphenyl]benzamide or a pharmaceutically acceptable salt thereof.

9. A compound of claim 1 which is N-{3-[2-(hepta-O-acetyl-β-D-maltosyloxymethyl)-6-methylphenylcarbamoyl]phenyl}-3,5-di-tert-butyl-4-hydroxybenzamide or a pharmaceutically acceptable salt thereof.

10. A compound of claim 1 which is N-[5-(hepta-O-acetyl-β-D-maltosyloxymnethyl)-2-methylphenyl]-3-cyanobenzamide or a pharmaceutically acceptable salt thereof.

11. A compound of claim 1 which is N-[5-(hepta-O-acetyl-β-D-maltosyloxymethyl)-2-methylphenyl]-5-nitroisophthalamic acid methyl ester or a pharmaceutically acceptable salt thereof.

12. A compound of claim 1 which is N-[5-(hepta-O-acetyl-β-D-maltosyloxymethyl)-2-methylphenyl]acetamide or a pharmaceutically acceptable salt thereof.

13. A compound of claim 1 which is N-[5-(hepta-O-acetyl-β-D-maltosyloxymethyl)-2-methylphenyl]propionamide or a pharmaceutically acceptable salt thereof.

14. A compound of claim 1 which is pentanoic acid N-[5-(Hepta-O-acetyl-β-D-maltosyloxymethyl)-2-methylphenyl]amide or a pharmaceutically acceptable salt thereof.

15. A compound of claim 1 which is N-[5-(hepta-O-acetyl-β-D-maltosyloxymethyl)-2-methylphenyl]-2,2-dimethylpropionamide or a pharmaceutically acceptable salt thereof.

16. A compound of claim 1 which is cyclopropanecarboxylic acid N-[5-(hepta-O-acetyl-β-D-maltosyloxymethyl)-2-methylphenyl]amide or a pharmaceutically acceptable salt thereof.

17. A compound of claim 1 which is cyclopentanecarboxylic acid N-[5-(hepta-acetyl-β-D-maltosyloxymethyl)-2-methylphenyl]anide or a pharmaceutically acceptable salt thereof.

18. A compound of claim 1 which is N-[5-(hepta-O-acetyl-β-D-maltosyloxymethyl)-2-methylphenyl]-3-cyclopentylpropionamide or a pharmaceutically acceptable salt thereof.

19. A compound of claim 1 which is N-[5-(hepta-O-acetyl-β-D-maltosyloxymethyl)-2-methylphenyl]-4-(methanesulfonylamino)benzenesulfonamide or a pharmaceutically acceptable salt thereof.

20. A compound of claim 1 which is N-[5-(hepta-O-acetyl-β-D-maltosyloxymethyl)-2-methylphenyl]-4-cyanobenzenesulfonamide or a pharmaceutically acceptable salt thereof.

21. A compound of claim 1 which is N-[5-(hepta-O-acetyl-β-D-maltosyloxymethyl)-2-methylphenyl]-4-trifluoromethylbenzenesulfonamide or a pharmaceutically acceptable salt thereof.

22. A compound of claim 1 which is N-[5-(hepta-O-acetyl-β-D-maltosyloxymethyl)-2-methylphenyl]-3-trifluoromethylbenzenesulfonamide or a pharmaceutically acceptable salt thereof.

23. A compound of claim 1 which is N-[5-(hepta-O-acetyl-β-D-maltosyloxymethyl)-2-methylphenyl]-2-trifluoromethylbenzenesulfonamide or a pharmaceutically acceptable salt thereof.

24. A compound of claim 1 which is N-[5-(hepta-O-acetyl-β-D-maltosyloxymethyl)-2-methylphenyl]-3-(methanesulfonylamino)benzenesulfonamide or a pharmaceutically acceptable salt thereof.

25. A compound of claim 1 which is N-[5-(hepta-O-acetyl-β-D-maltosyloxymethyl)-2-methylphenyl]-4-methoxybenzenesulfonamide or a pharmaceutically acceptable salt thereof.

26. A compound of claim 1 which is N-[5-(hepta-O-acetyl-β-D-maltosyloxymethyl)-2-methylphenyl]-4-methylbenzenesulfonamide or a pharmaceutically acceptable salt thereof.

27. A compound of claim 1 which is N-[5-(hepta-O-acetyl-β-D-maltosyloxymethyl)-2-methylphenyl]-4-chlorobenzenesulfonamide or a pharmaceutically acceptable salt thereof.

28. A compound of claim 1 which is N-[5-(hepta-O-acetyl-β-D-maltosyloxymethyl)-2-methylphenyl]-4-chloro-3-nitrobenzenesulfonamide or a pharmaceutically acceptable salt thereof.

29. A compound of claim 1 which is N-[5-(hepta-O-acetyl-β-D-maltosyloxymethyl)-2-methylphenyl]methanesulfonamide or a pharmaceutically acceptable salt thereof.

30. A compound of claim 1 which is butane-1-sulfonic acid N-[5-(hepta-O-acetyl-β-D-maltosyloxymethyl)-2-methylphenyl]amide or a pharmaceutically acceptable salt thereof.

31. A compound of claim 1 which is 4-(hepta-O-acetyl-β-D-maltosyloxymethyl)-2-methylphenylamine hydrochloride or a pharmaceutically acceptable salt thereof.

32. A compound of claim 1 which is N-[4-(hepta-O-acetyl-β-D-maltosyloxymethyl)-2-methylphenyl]-4-(methanesulfonylamnino)benzenesulfonamide or a pharmaceutically acceptable salt thereof.

33. A compound of claim 1 which is N-[4-(hepta-O-acetyl-β-D-maltosyloxymethyl)-2-methylphenyl]-4-nitro-N-(4-nitrophenylsulfonyl)benzenesulfonamide or a pharmaceutically acceptable salt thereof.

34. A compound of claim 1 which is N-acetyl-4-[acetyl(methanesulfonyl)amino]-N-[5-(4',6'-O-isopropylidine-2,2',3,3',6-penta-O-acetyl-β-D-maltosyloxymethyl)-2-methylphenyl]benzenesulfonamide or a pharmaceutically acceptable salt thereof.

35. A compound of claim 1 which is N-propionyl-4-[propionyl(methanesulfonyl)amino]-N-[5-(hepta-O-propionyl-β-D-maltosyloxymethyl)-2-methylphenyl]benzenesulfonamide or a pharmaceutically acceptable salt thereof.

36. A method of treating a human suffering from a condition which is characterized by excessive smooth muscle proliferation, the method comprising administering to the human an effective amount of a compound of formula I

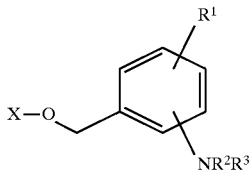

where X is

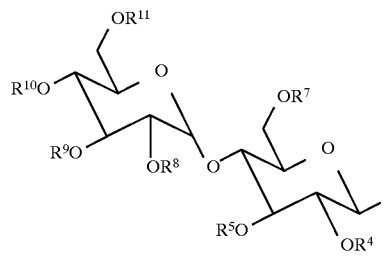

or

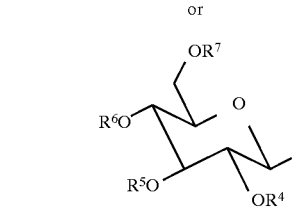

$R^1$ is H, alkyl having 1 to 6 carbon atoms, halo, $CF_3$, CN, $NO_2$, or alkoxy having 1 to 6 carbon atoms;

$R^2$ is H, an acyl group having 1 to 6 carbon atoms, phenylsulfonyl, or phenylsulfonyl substituted with $NO_2$; and $R^3$ is H, an acyl group having 1 to 8 carbon atoms, alkylsulfonyl having 1 to 6 carbon atoms, benzoyl, benzoyl substituted with $NH_2$, $NO_2$, CN, $C_1$–$C_6$ alkyl, $C_1$–$C_6$ alkoxy, $C_2$–$C_{15}$ acylamino, $CF_3$, $C_1$–$C_6$ alkanesulfonylamino, acetyl(methanesulfonyl)amino, halo, or OH, phenylsulfonyl, or phenylsulfonyl substituted with $C_1$–$C_6$ alkyl, $C_1$–$C_6$ alkoxy, $C_2$–$C_{15}$ acylamino, $NO_2$, CN, $CF_3$, $C_1$–$C_6$ alkanesulfonylamino, acetyl(methanesulfonyl)amino, OH, or halo;

$R^4$, $R^5$, $R^6$, $R^7$, $R^8$, and $R^9$ are each, independently, an acyl group having 1 to 6 carbon atoms; and $R^{10}$ and $R^{11}$ are each, independently, an acyl group having 1 to 6 carbon atoms, or the $R^{10}$ and $R^{11}$ groups on the 4' and 6' positions of the maltose or the 4 and 6 positions of the glucose form an isopropylidene group;

or a pharmaceutically acceptable salt thereof.

37. The method of claim 36 in which the condition which is characterized by excessive smooth muscle proliferation is restenonsis.

38. A pharmaceutical composition comprising an effective amount of a compound of formula I

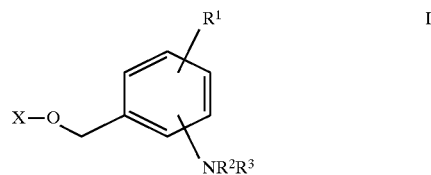

where X is

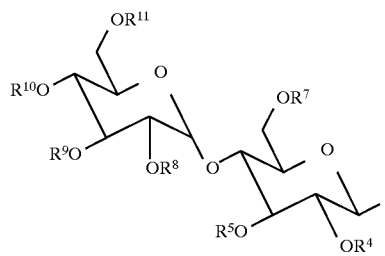

or

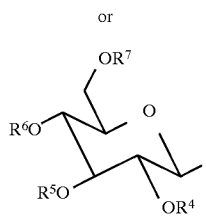

$R^1$ is H, alkyl having 1 to 6 carbon atoms, halo, $CF_3$, CN, $NO_2$, or alkoxy having 1 to 6 carbon atoms;

$R^2$ is H, an acyl group having 1 to 6 carbon atoms, phenylsulfonyl, or phenylsulfonyl substituted with $NO_2$; and $R^3$ is H, an acyl group having 1 to 8 carbon atoms, alkylsulfonyl having 1 to 6 carbon atoms, benzoyl, benzoyl substituted with $NH_2$, $NO_2$, CN, $C_1$–$C_6$ alkyl, $C_1$–$C_6$ alkoxy, $C_2$–$C_{15}$ acylamino, $CF_3$, $C_1$–$C_6$ alkanesulfonylamino, acetyl(methanesulfonyl)amino, halo, or OH, phenylsulfonyl, orphenylsulfonyl substituted with $C_1$–$C_6$ alkyl, $C_1$–$C_6$ alkoxy, $C_2$–$C_{15}$ acylamino, $NO_2$, CN, $CF_3$, $C_1$–$C_6$ alkanesulfonylamino, acetyl(methanesulfonyl)amino, OH, or halo;

$R^4$, $R^5$, $R^6$, $R^7$, $R^8$, and $R^9$ are each, independently, an acyl group having 1 to 6 carbon atoms; and $R^{10}$ and $R^{11}$ are each, independently, an acyl group having 1 to 6 carbon atoms, or the $R^{10}$ and $R^{11}$ groups on the 4' and 6' positions of the maltose or the 4 and 6 positions of the glucose form an isopropylidene group;

or a pharmaceutically acceptable salt thereof and a pharmaceutically acceptable excipient.

* * * * *

UNITED STATES PATENT AND TRADEMARK OFFICE
CERTIFICATE OF CORRECTION

PATENT NO. : 5,773,420

DATED : June 30, 1998

INVENTORS : Thomas T. Nguyen
John W. Ellingboe

It is certified that an error appears in the above-identified patent and that said Letters Patent is hereby corrected as shown below:

On the title page, please insert - -

Related U.S. Application Data

-- [63] Continuation-in-part of Ser. No. 335,286, Nov. 7, 1994, abandoned. - -

Col. 1, line 5, immediately after the title, insert - - This application is a continuation-in-part of U.S. Serial No. 08/335,286, filed November 7, 1994, now abandoned. - -

Signed and Sealed this

Fourth Day of May, 1999

*Attest:*

Q. TODD DICKINSON

*Attesting Officer*     *Acting Commissioner of Patents and Trademarks*